United States Patent
Stuurman

(10) Patent No.: US 11,266,115 B2
(45) Date of Patent: Mar. 8, 2022

(54) METHODS FOR THE PRODUCTION OF SEED WITH IMPROVED SEED GERMINATION PROPERTIES

(71) Applicant: Keygene N.V., Wageningen (NL)

(72) Inventor: Jeroen Stuurman, Wageningen (NL)

(73) Assignee: KEYGENE N.V., Wageningen (NL)

( * ) Notice: Subject to any disclaimer, the term of this patent is extended or adjusted under 35 U.S.C. 154(b) by 47 days.

(21) Appl. No.: 16/449,334

(22) Filed: Jun. 21, 2019

(65) Prior Publication Data

US 2020/0045925 A1    Feb. 13, 2020

Related U.S. Application Data

(63) Continuation of application No. PCT/EP2017/084301, filed on Dec. 22, 2017.

(30) Foreign Application Priority Data

Dec. 23, 2016 (NL) .................................. 2018059

(51) Int. Cl.
*A01H 5/08* (2018.01)
*A01H 1/04* (2006.01)
*A01H 5/10* (2018.01)
*A01H 6/82* (2018.01)

(52) U.S. Cl.
CPC .............. *A01H 6/825* (2018.05); *A01H 1/04* (2013.01); *A01H 5/08* (2013.01); *A01H 5/10* (2013.01)

(58) Field of Classification Search
None
See application file for complete search history.

(56) References Cited

FOREIGN PATENT DOCUMENTS

EP    2 128 255 A1    12/2009

OTHER PUBLICATIONS

Marcotrigiano et al., The Plant Journal, 1995, vol. 7, No. 2, pp. 193-202.*
Burge et al. "Opportunities for synthetic plant chimeral breeding: Past and future." Plant cell, tissue and organ culture 70.1 (2002): 13-21.
Filippis et al. "Using a periclinal chimera to unravel layer-specific gene expression in plants." The Plant Journal 75.6 (2013): 1039-1049.
International Search Report dated Mar. 27, 2018 for International Patent Application No. PCT/EP2017/084301 filed Dec. 22, 2017. 8 pages.
Lindsay et al. "Graft chimeras and somatic hybrids for new cultivars." New Zealand Journal of Botany 33.1 (1995): 79-92.
Nassar et al. "Interspecific Periclinal Chimeras as a Strategy for Cultivar Development." Plant Breeding Reviews 40 (2016): 235-269.
Nozawa et al. "Synthesis and utilization of in vitro artificially synthesized chimeras." Combined Proceedings of the International Plant Propagators' Society. vol. 52 (2002): 346.
Satina et al. "Demonstration of the three germ layers in the shoot apex of Datura by means of induced polyploidy in periclinal chimeras." American Journal of Botany 27.10 (1940): 895-905.
Szymkowiak et al. "The internal meristem layer (L3) determines floral meristem size and carpel number in tomato periclinal chimeras." The Plant Cell 4.9 (1992): 1089-1100.

* cited by examiner

*Primary Examiner* — Phuong T Bui
(74) *Attorney, Agent, or Firm* — Sunit Talapatra; Foley & Lardner LLP

(57) ABSTRACT

The present invention provides methods for the production of plant inbred seed, or for the production of plant hybrid seed, wherein the seed obtained exhibits altered and/or improved germination properties, in particular improved germination properties such as enhanced seed germination rate, enhanced seed germination capacity and/or enhanced seedling fresh weight. The present invention also provides for the use of periclinal chimera plants for improving germination properties of seed.

11 Claims, 17 Drawing Sheets

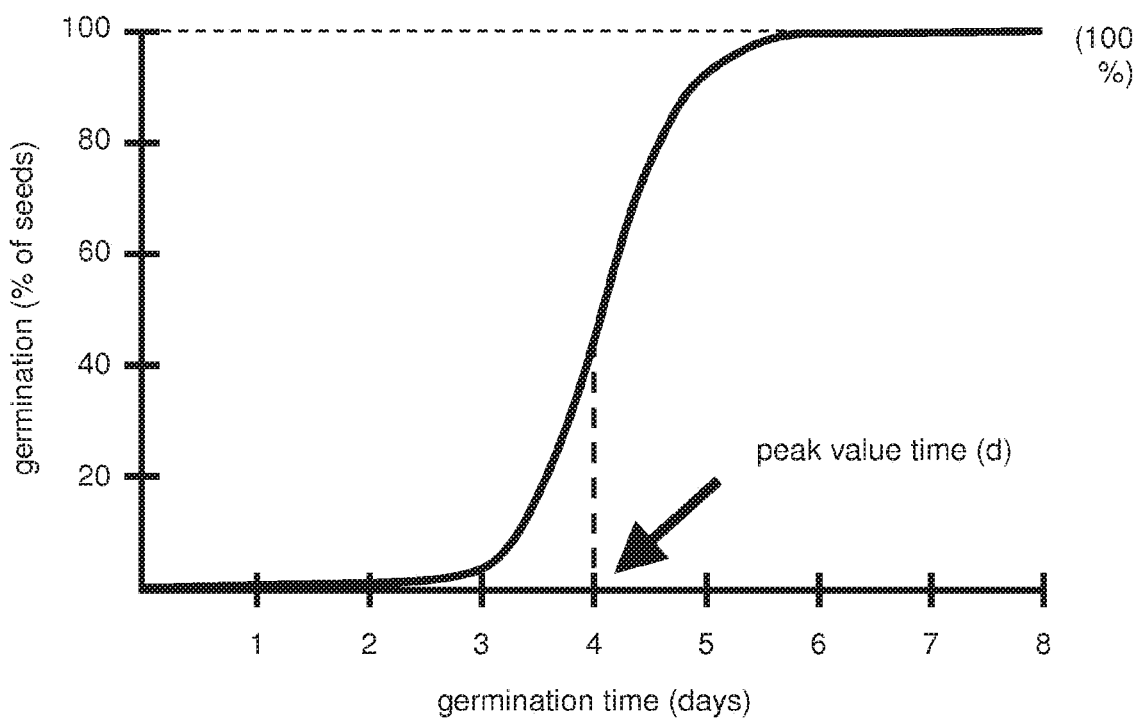

METHODS FOR THE PRODUCTION OF SEED WITH IMPROVED SEED GERMINATION PROPERTIES

CROSS-REFERENCE TO RELATED PATENT APPLICATIONS

This application is a continuation of International Patent Application No. PCT/EP2017/084301, filed Dec. 22, 2017, which claims the benefit of and priority to Netherlands Application No. 2018059, filed Dec. 23, 2016. The entire disclosure of each application is incorporated by reference herein.

FIELD OF THE INVENTION

The present invention relates to the field of agriculture. In particular, the present invention relates to seed production, and to methods of improving the quality of seeds produced, in particular methods of improving seed germination properties.

BACKGROUND OF THE INVENTION

The standard solution to enhance crop traits has been genetics and breeding. However, classical breeding techniques can have as side effect that properties of seeds are affected. For instance for tomato, a significant proportion of new F1-hybrids do not enter the market because of inferior seed quality, i.e. inferior seed germination capacity, seed germination uniformity, seed germination rate and/or seedling fresh weight and vigour, which means a substantial loss of research investments to the plant breeding industry, and hampering of progress in breeding. It is necessary for hybrid seeds to germinate at least to 80-85% in order for it to be commercially viable after priming. It is of primary concern for a seed company not only to improve plant traits, but also to produce seed with good germination properties.

For example, high fruit or leaf yield, or exaggerated/semi-natural characters such as very large fruit size in beef tomatoes, may show a negative pleiotropic effect on seed quality, which may amongst other possibilities result from unfavourable assimilate partitioning away from the developing seed, and resulting in low seed germination capacity, seed germination uniformity, seed germination rate and/or seedling fresh weight and vigour. In such case, a balance must be sought between plant output traits and seed traits, with both aspects negatively compromised.

Where seed quality may in principle be improved by breeding, it will be time-consuming and difficult, and, most importantly, it may affect other desirable genomic properties. As a quantitative trait, it will require the introduction of multiple favourable loci into a desired genome. Particularly in breeding germplasm wherein seed quality has been neglected as a target of selection, the necessity to re-acquire good seed germination properties will be a major setback in the breeding programs.

Thus, there is an urgent need in the art to improve properties of seeds—like seed germination capacity, seed germination uniformity, seed germination rate and/or seedling fresh weight and vigour—produced by plants, without interfering with the genetic composition of the inbred or hybrid seeds, which were developed in order to produce plants with desired agronomic or horticultural traits, and without the need to go back into the pedigrees and correct the seed quality deficits by classical breeding and selection.

Solution Provided by the Present Invention

The present inventor has come to the insight that a solution to the above-mentioned problems can be provided by producing seed of an existing commercial inbred line or F1-hybrid cultivar within the fruits of another cultivar making use of a periclinal chimera plant. Because this production system does not require an adaptation in the genetics of the particular cultivars used, the above-mentioned problems of the standard solution involving breeding and/or genetics are overcome.

It is known that the L2-shoot meristem layer of a periclinal chimera plant determines the genotype of the gametes (e.g. Filippis et al. *Using a periclinal chimera to unravel layer-specific gene expression in plants*, The Plant Journal, 2013, 75: 1039-1049). Further, preliminary investigations were done to investigate the usefulness of this technology in the provision of new cultivars, for instance by making chimera of nightshade and tomato using, however, with disappointing results (Lindsay et al. *Graft chimeras and somatic hybrids for new cultivars*, New Zealand journal of Botany, 1995, Vol. 33: 79-92).

Surprisingly, it was found that the germination properties of seed can be enhanced dramatically by altering the genotype of the L1 and/or L3-shoot meristem layer of the female parent without changing the genotype of the resulting seed. This enhancement may mean that a commercially unprofitable hybrid line may become commercially viable. During the production of sowing seed, the health and vigour of the maternal plant (i.e. the one that carries the seed as its offspring) is instrumental to obtain a good quality of seeds. This is true for all production systems, whether they are based on the production of inbred seed or F1-hybrid seed, and the invention provides a solution with a very general applicability, i.e. a simple procedure is provided that allows the immediate commercial production of superior quality seeds of any inbred or F1-hybrid cross, of old as well as new varieties. According to the inventive concept, seed is produced on a deliberately chosen distinct mother plant, solely selected for its maternal properties to support optimal seed development, i.e. resulting in seed with improved seed quality, for example improved germination rate, germination capacity, and/or seedling fresh weight, while avoiding the severe drawbacks of the prior art technology and interference of the valuable genetic composition of the desired inbred or hybrid seeds.

SUMMARY OF THE INVENTION

The present inventor has found a way of producing seed by first making a periclinal chimera plant, and subsequently producing seed on such a plant. In this way, the phenotypic properties of the seed produced on the plant are improved, in particular the germination properties of said seed, such as germination rate, germination capacity and/or seedling fresh weight, are improved compared to seed produced in a fruit of its own genotype.

The present disclosure teaches the methods, uses, aspects and embodiments as represented in the following clauses:

Clause 1

Method for the production of seed with an embryo genotype identical to seed obtained by crossing a first plant A with a second plant B, wherein one or more germination properties of the seed are altered and/or improved, compared to seed obtained by crossing plants A and B, the method comprising:

a) making or providing a periclinal chimera plant comprising an L2-shoot meristem layer that has the genotype of plant A, and an L1-shoot meristem layer that has the genotype of a third plant C;
b) pollinating the periclinal chimera plant with pollen of plant B;
c) harvesting the seed thus obtained.

Clause 2

Method for the production of seed with an embryo genotype identical to seed obtained by crossing a first plant A with a second plant B, wherein one or more germination properties of the seed are altered and/or improved, compared to seed obtained by crossing plants A and B, the method comprising:
a) making or providing a periclinal chimera plant comprising an L2-shoot meristem layer that has the genotype of plant A, and an L3-shoot meristem layer that has the genotype of a third plant C;
b) pollinating the periclinal chimera plant with pollen of plant B;
c) harvesting the seed thus obtained.

Clause 3

Method for altering and/or improving one or more germination properties of a seed with an embryo genotype identical to seed obtained by crossing a first plant A with a second plant B, the method comprising:
a) making or providing a periclinal chimera plant comprising an L2-shoot meristem layer that has the genotype of plant A, and an L1-shoot meristem layer that has the genotype of a third plant C;
b) pollinating the periclinal chimera plant with pollen of plant B;
c) harvesting the seed thus obtained.

Clause 4

Method for altering and/or improving one or more germination properties of a seed with an embryo genotype identical to seed obtained by crossing a first plant A with a second plant B, the method comprising:
a) making or providing a periclinal chimera plant comprising an L2-shoot meristem layer that has the genotype of plant A, and an L3-shoot meristem layer that has the genotype of a third plant C;
b) pollinating the periclinal chimera plant with pollen of plant B;
c) harvesting the seed thus obtained.

Clause 5 Method for altering and/or improving one or more germination properties of a seed with an embryo genotype identical to seed obtained by crossing a first plant A with a second plant B as compared to the germination properties of seed obtained by crossing plants A and B, the method comprising:
a) making or providing a periclinal chimera plant comprising an L2-shoot meristem layer that has the genotype of plant A, and an L1-shoot meristem layer that has the genotype of a third plant C;
b) pollinating the periclinal chimera plant with pollen of plant B;
c) harvesting the seed thus obtained.

Clause 6

Method for altering and/or improving one or more germination properties of a seed with an embryo genotype identical to seed obtained by crossing a first plant A with a second plant B as compared to the germination properties of seed obtained by crossing plants A and B, the method comprising:
a) making or providing a periclinal chimera plant comprising an L2-shoot meristem layer that has the genotype of plant A, and an L3-shoot meristem layer that has the genotype of a third plant C;
b) pollinating the periclinal chimera plant with pollen of plant B;
c) harvesting the seed thus obtained.

Clause 7

Method for assessing at least one germination property of seed with an embryo genotype identical to seed obtained by crossing a first plant A with a second plant B, wherein one or more germination properties of the seed are altered and/or improved, the method comprising:
a) making or providing a periclinal chimera plant comprising an L2-shoot meristem layer that has the genotype of plant A, and an L1-shoot meristem layer that has the genotype of a third plant C;
b) pollinating the periclinal chimera plant with pollen of plant B;
c) harvesting the seed thus obtained; and
d) assessing at least one germination property of the seed obtained in step c).

Clause 8

Method for assessing at least one germination property of seed with an embryo genotype identical to seed obtained by crossing a first plant A with a second plant B, wherein one or more germination properties of the seed are altered and/or improved, the method comprising:
a) making or providing a periclinal chimera plant comprising an L2-shoot meristem layer that has the genotype of plant A, and an L3-shoot meristem layer that has the genotype of a third plant C;
b) pollinating the periclinal chimera plant with pollen of plant B;
c) harvesting the seed thus obtained; and
d) assessing at least one germination property of the seed obtained in step c).

Clause 9

Method for germinating seed with an embryo genotype identical to seed obtained by crossing a first plant A with a second plant B, wherein one or more germination properties of the seed are altered and/or improved, the method comprising:
a) making or providing a periclinal chimera plant comprising an L2-shoot meristem layer that has the genotype of plant A, and an L1-shoot meristem layer that has the genotype of a third plant C;
b) pollinating the periclinal chimera plant with pollen of plant B;
c) harvesting the seed thus obtained; and
d) allowing the seed obtained in step c) to germinate; and,
e) optionally assessing at least one germination property of the seed obtained in step c).

Clause 10

Method for germinating seed with an embryo genotype identical to seed obtained by crossing a first plant A with a second plant B, wherein one or more germination properties of the seed are altered and/or improved, the method comprising:
a) making or providing a periclinal chimera plant comprising an L2-shoot meristem layer that has the genotype of plant A, and an L3-shoot meristem layer that has the genotype of a third plant C;
b) pollinating the periclinal chimera plant with pollen of plant B;
c) harvesting the seed thus obtained; and
d) allowing the seed obtained in step c) to germinate; and, e) optionally assessing at least one germination property of the seed obtained in step c).

Clause 11

Use of a periclinal chimera plant for altering and/or improving one or more germination properties of a seed with an embryo genotype identical to seed obtained by crossing a first plant A with a second plant B, wherein the periclinal chimera plant comprises an L2-shoot meristem layer that has the genotype of plant A, and an L1-shoot meristem layer that has the genotype of a third plant C.

Clause 12

Use of a periclinal chimera plant for altering and/or improving one or more germination properties of a seed with an embryo genotype identical to seed obtained by crossing a first plant A with a second plant B, wherein the periclinal chimera plant comprises an L2-shoot meristem layer that has the genotype of plant A, and an L3-shoot meristem layer that has the genotype of a third plant C.

Clause 13

Use of a periclinal chimera plant for altering and/or improving one or more germination properties of a seed with an embryo genotype identical to seed obtained by crossing a first plant A with a second plant B, wherein the periclinal chimera plant comprises an L2-shoot meristem layer that has the genotype of plant A, and an L1-shoot meristem layer that has the genotype of a third plant C.

Clause 14

Use of a periclinal chimera plant for altering and/or improving one or more germination properties of a seed with an embryo genotype identical to seed obtained by crossing a first plant A with a second plant B, wherein the periclinal chimera plant comprises an L2-shoot meristem layer that has the genotype of plant A, and an L3-shoot meristem layer that has the genotype of a third plant C.

Clause 15

Use of a periclinal chimera plant for the production of seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L1-shoot meristem layer that has the genotype of a third plant C.

Clause 16

Use of a periclinal chimera plant for the production of seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L3-shoot meristem layer that has the genotype of a third plant C.

Clause 17

Use of a periclinal chimera plant for the production of seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L1-shoot meristem layer that has the genotype of a third plant C.

Clause 18

Use of a periclinal chimera plant for the production of seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L3-shoot meristem layer that has the genotype of a third plant C.

Clause 19

Use of a periclinal chimera plant for assessing one or more germination properties of a seed with an embryo genotype identical to seed obtained by crossing a first plant A with a second plant B, wherein the periclinal chimera plant comprises an L2-shoot meristem layer that has the genotype of plant A, and an L1-shoot meristem layer that has the genotype of a third plant C.

Clause 20

Use of a periclinal chimera plant for assessing one or more germination properties of a seed with an embryo genotype identical to seed obtained by crossing a first plant A with a second plant B, wherein the periclinal chimera plant comprises an L2-shoot meristem layer that has the genotype of plant A, and an L3-shoot meristem layer that has the genotype of a third plant C.

Clause 21

Use of a periclinal chimera plant for assessing one or more germination properties of a seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L1-shoot meristem layer that has the genotype of a third plant C.

Clause 22

Use of a periclinal chimera plant for assessing one or more germination properties of a seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L3-shoot meristem layer that has the genotype of a third plant C.

Clause 23

Use of a periclinal chimera plant for germination of a seed with an embryo genotype identical to seed obtained by crossing a first plant A with a second plant B, wherein the periclinal chimera plant comprises an L2-shoot meristem layer that has the genotype of plant A, and an L1-shoot meristem layer that has the genotype of a third plant C.

Clause 24

Use of a periclinal chimera plant for germination of a seed with an embryo genotype identical to seed obtained by crossing a first plant A with a second plant B, wherein the periclinal chimera plant comprises an L2-shoot meristem layer that has the genotype of plant A, and an L3-shoot meristem layer that has the genotype of a third plant C.

Clause 25

Use of a periclinal chimera plant for germination of a seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L1-shoot meristem layer that has the genotype of a third plant C.

Clause 26

Use of a periclinal chimera plant for germination of a seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L3-shoot meristem layer that has the genotype of a third plant C.

Clause 27

The method or use according to any one of the previous clauses, wherein in the periclinal chimera plant the L1- and L3-shoot meristem layer both have the genotype of the third plant C.

Clause 28

The method or use according to any one of the previous clauses, wherein the genotype of plant A is identical to the genotype of plant B or is identical to the genotype of the L2-layer of plant B.

Clause 29

The method or use according to any one of the previous clauses, wherein the genotype of plant A differs from the genotype of plant B or differs from the genotype of the L2-layer of plant B.

Clause 30

Method or use according any one of the previous clauses, wherein the one or more germination properties are selected from the group consisting of seed density, seed biomass, seed germination rate, seed germination capacity and seedling fresh weight.

Clause 31

Method or use according to clause 30, wherein seed germination rate, seed germination capacity and/or seedling fresh weight are enhanced as compared to seed obtained by crossing a first plant A with a second plant B.

Clause 32

Method or use according to any one of the previous clauses, wherein said second plant B is a non-chimeric plant.

Clause 33

Method or use according to any one of the previous clauses, wherein said first plant A and said third plant C are from the same species.

Clause 34

Method or use according to any one of the previous clauses, wherein said first plant A, said second plant B, and said third plant C are all from the same species.

Clause 35

Method or use according to clause 33 or 34, wherein said plants are from species belonging to the genus *Solanum*.

Clause 36

Method or use according to clause 35, wherein said third plant C is tomato variety Ailsa Craig.

Clause 37

Method or use according to any one of the previous clauses, wherein said third plant C produces seed with enhanced germination rate, germination capacity and/or seedling fresh weight compared to seed produced by said first plant A.

Clause 38

Method for the production of tomato seed with an embryo genotype identical to seed obtained by crossing a first tomato plant A with a second tomato plant B, wherein one or more germination properties of the seed are altered and/or improved, compared to seed obtained by crossing plants A and B, the method comprising:

a) making a periclinal chimera tomato plant comprising an L2-shoot meristem layer that has the genotype of tomato plant A, and an L1-shoot meristem layer that has the genotype of tomato variety Ailsa Craig;

b) pollinating the periclinal chimera plant with pollen of tomato plant B;

c) harvesting the seed thus obtained.

Clause 39

Method according to clause 38, wherein the genotype of tomato plant A is identical to the genotype of tomato plant B.

Clause 40

Method according to clause 38 or 39, wherein plant A is a beef tomato.

Clause 41

Method according to clauses 38, 39 or 40, wherein germination rate, germination capacity and/or seedling fresh weight are enhanced as compared to seed obtained by crossing a first plant A with a second plant B.

Clause 42

Use of a periclinal chimera plant for the production of seed with an embryo genotype identical to seed obtained by crossing a first plant A with a second plant B, wherein one or more germination properties are altered and/or improved, as compared to the germination properties of seed obtained by crossing plants A and B, wherein the periclinal chimera plant comprises an L2-shoot meristem layer that has the genotype of plant A, and an L1-shoot meristem layer that has the genotype of a third plant C.

Clause 43

Seed obtained or obtainable by a method of any of the above clauses, wherein said seed has at least one altered and/or improved germination property as compared to the seed obtained or obtainable by crossing plant A with plant B, wherein plant A and B are as defined in the above clauses.

Clause 44

Seed according to clause 43, wherein said seed has an integument or seed coat that has the genotype of the L1-layer of the periclinal chimera plant, wherein the periclinal chimera plant is the periclinal chimera plant as defined in the above clauses.

A first plant A (also denominated herein as "plant A") and a third plant C (also denominate herein as "plant C") are to be understood herein as non-chimeric plants, i.e. having the same genotype for all three meristem layers L1, L2 and L3. The second plant B (also denominated herein as "plant B"), may be a chimeric or a non-chimeric plant. In cases wherein plant B is a chimeric plant, "the genotype of plant B" is to be construed herein as "the genotype of the L2-layer of plant B". Crossing a first plant A with a second plant B is to be understood herein as crossing a first plant A as female plant with a second plant B as male plant. The genotype of plant A and/or the genotype of plant C referred to in the clauses above can be any inbred or hybrid genotype. Such a hybrid or inbred can comprise for instance about 0.5, 1, 2, 5, 7, 10, 15, 20, 25, 30, 40 or 50% of the genotype of one of the partners in the hybridization cross. The genotype of plant C may comprise part of the genotype of plant A and/or plant B. For instance, plant C may be a hybrid of the first or a inbred of further generation resulting from a cross of plant A and/or plant B. The L1 and/or L3-shoot meristem layer of the periclinal chimera plant may have the genotype of a hybrid or inbred of the first or a further generation resulting from a cross of plant A and/or plant B.

The genotype of plant A and/or the genotype of plant C referred to in the clauses above can be haploid, diploid, aneuploid or polyploid.

Plant A, plant B, and plant C as used herein may be replaced by plant of line A, plant of line B, and/or plant of line C, but not necessarily so.

The altered or improved germination properties of the seed are for instance a higher germination capacity, a more uniform germination, a higher germination rate, and/or an increased seedling biomass or fresh weight or vigour. Further altered or improved germination properties may be seed specific weight or seed biomass. The choice of the L1- and/or L3-shoot meristem layer, determines which of the one or more germination properties are improved. Given the phenotypic properties of non-chimeric plants, more in particular the germination properties, of seed obtained from such plants, using the knowledge of the present invention the skilled person knows what choice of shoot meristem layers (i.e. derived from which plant) to make in order to produce the periclinal chimera plant of the invention. In particular, the skilled person knows what choice of L1- and/or L3-shoot meristem layer to make in order to convey favourable germination characteristics on the seed produced.

The invention also provides for inbred seed, or hybrid seed, by the use of the periclinal chimera plant of the invention and as defined in step a of the clauses above. In a particular embodiment, the periclinal chimera plant of the invention is self-fertilized for seed production.

In a preferred embodiment, the genotype of the stem cells of the L3-shoot meristem layer is identical to the genotype of the stem cells of the L1-shoot meristem layer in the periclinal chimera plant of the invention.

DESCRIPTION OF THE DRAWINGS

FIG. 2. Figure to illustrate the concept of peak value time. The peak value time is the point in time at which the tangent of the germination curve is steepest, i.e. at which the increase of germinating seeds per unit time is highest. Peak value time, being a time point related to the dynamics of the germination, can be used to define the time period needed to assess the germination capacity, e.g. a time period equal to 2, 3, 4 or 5 times, preferably 3 times the time span from seed planting to peak value time.

Panel C. In vivo germination capacity. Left: XZ hybrid seed from a non-chimeric XX mother. Right: XZ hybrid seed from the chimera.

Figure 7A:
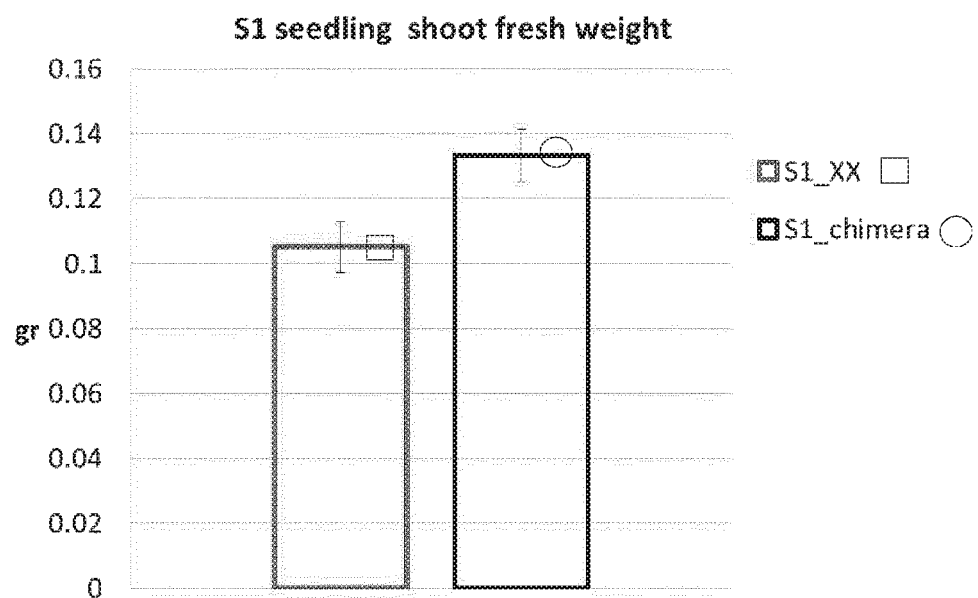
Figure 7B:
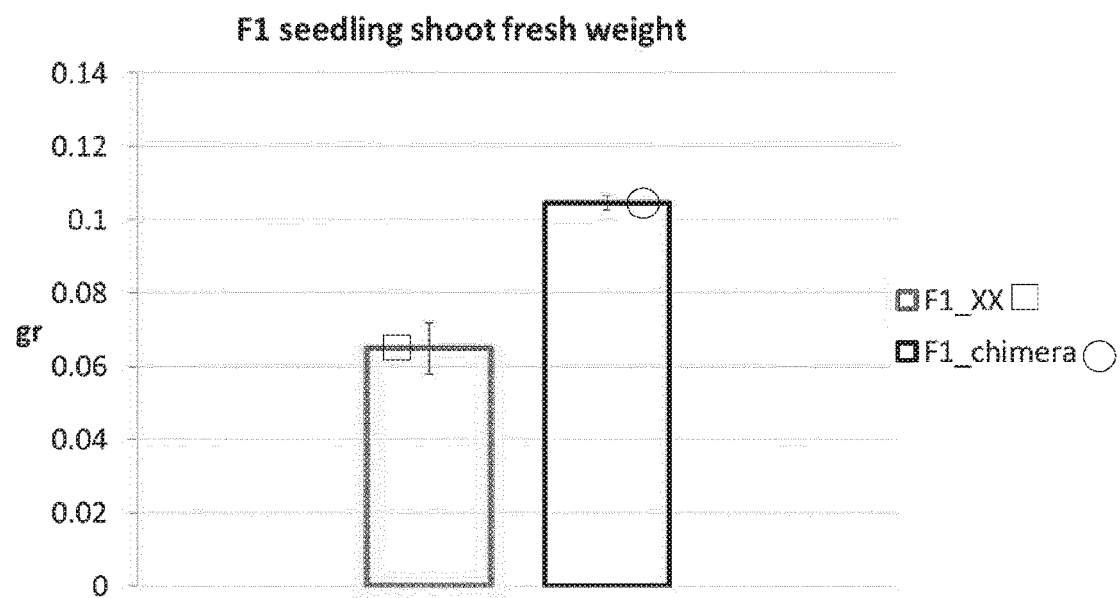

FIGS. 7A-7B. Seedling shoot fresh weight Error bars indicate the 95% confidence intervals. A: left column represents S1_XX, right column represents S1_chimera. B: left column represents F1_XX, right column represents F1_chimera.

Figure 8:
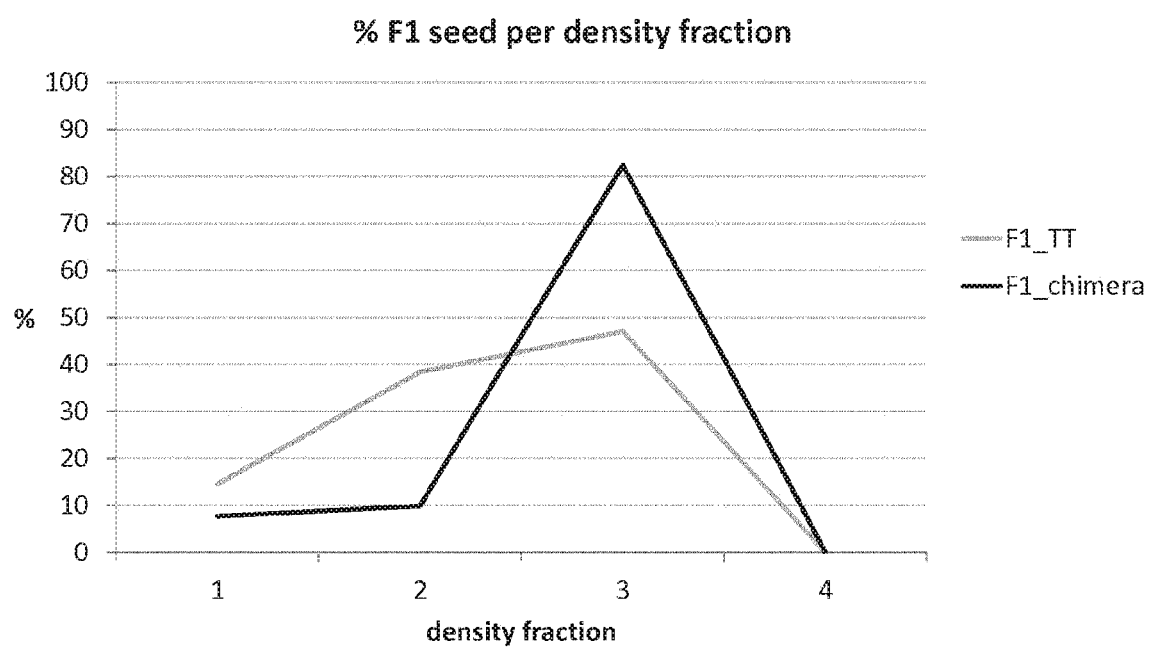

FIG. 8. Density distribution of seeds. At density class "3", the lines represent from top to bottom: F1_chimera (progeny of the cross-fertilization of the chimera with line PP) and F1_TT (progeny of the cross-fertilization of the non-chimeric plant TT with line PP).

Figure 9:
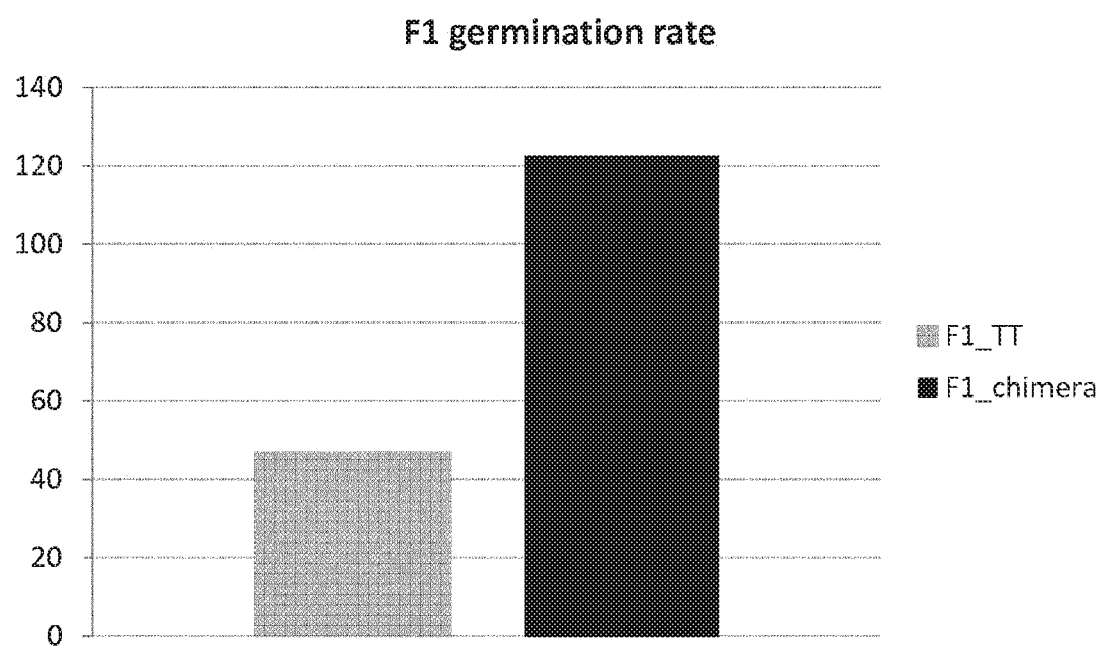

FIG. 9. Germination rate of seeds. Left column represents F1_TT, right column represents F1_chimera.

Figure 10:
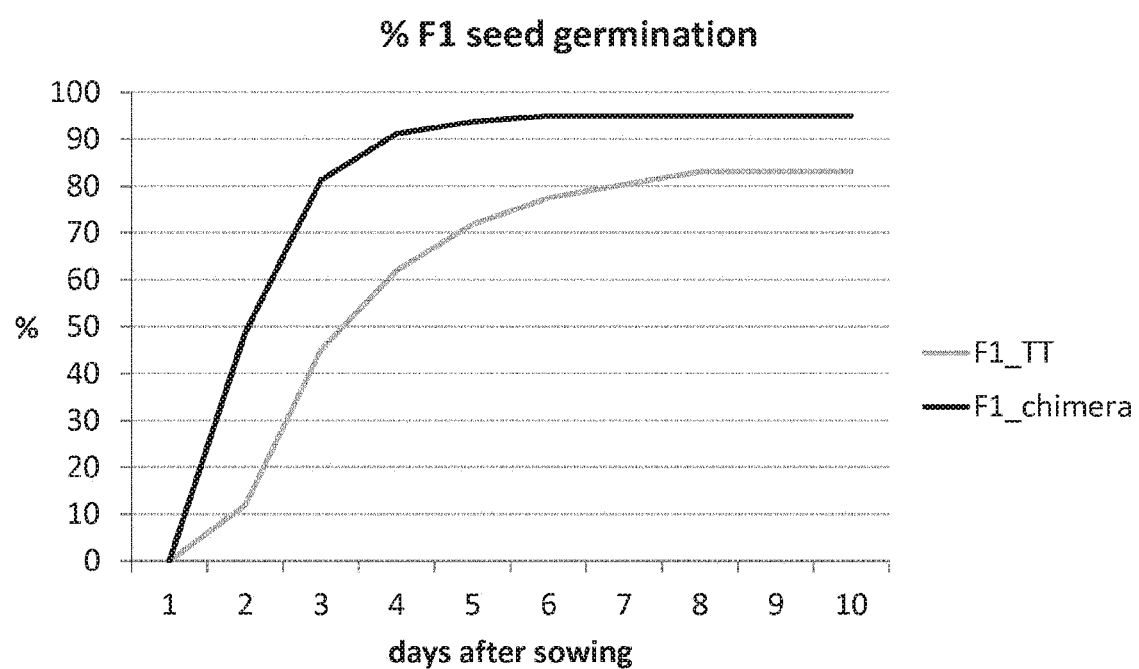

FIG. 10. In vitro germination capacity. Top line represents F1_chimera, bottom line represents F1_TT.

Figure 11:
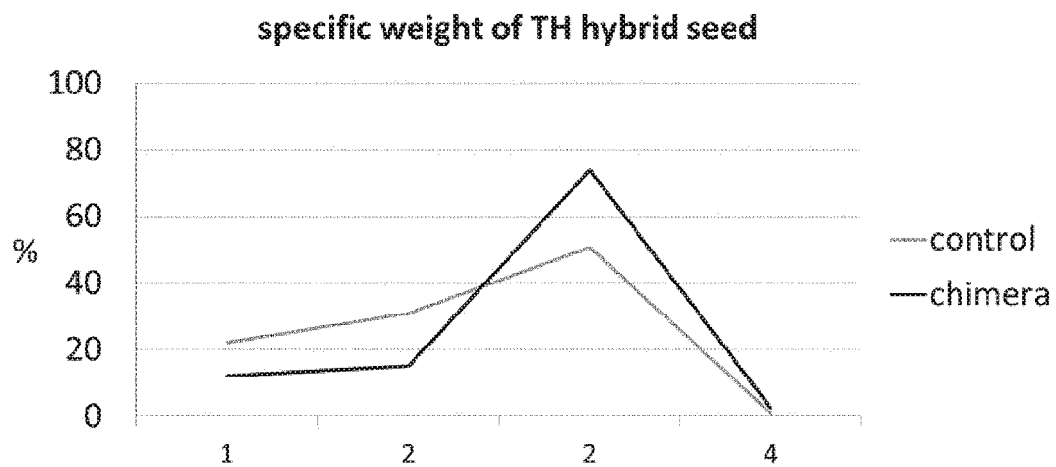

FIG. 11. Specific weight of TH hybrid seed. Black line represents F1_chimera (chimera; progeny of the cross-fertilization of the chimera with line HH), grey line represents F1_TT (control; progeny of the cross-fertilization of TT with line HH).

Figure 12:
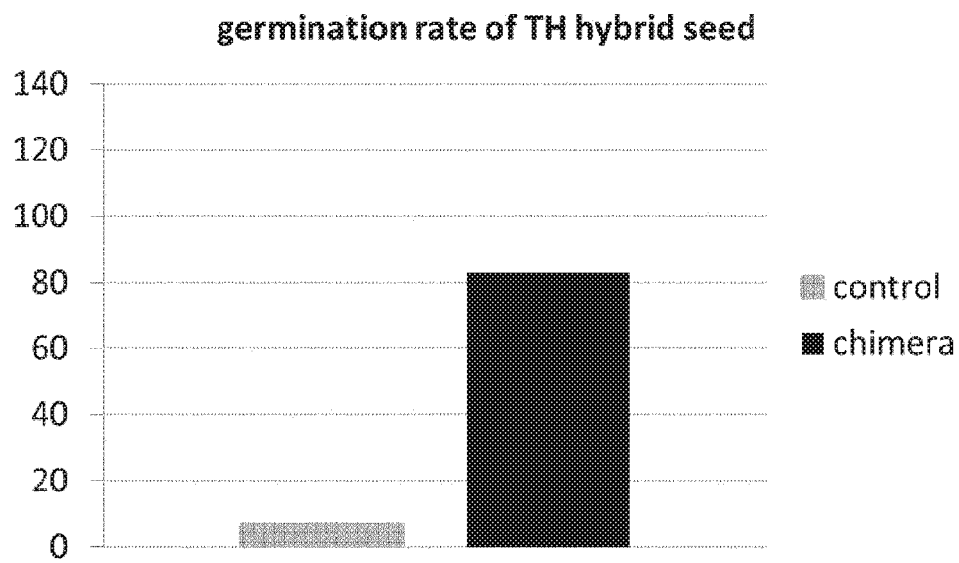

FIG. 12. Germination rate of TH hybrid seed. Black column represents F1_chimera, grey column represent F1_TT.

Figure 13:
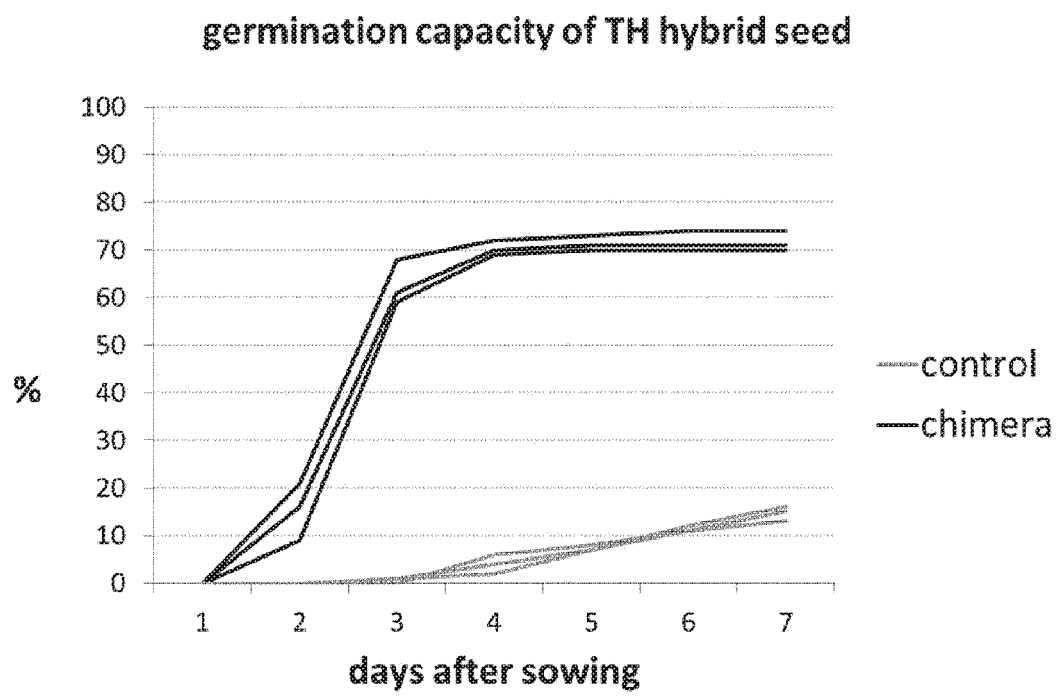

FIG. 13. In vitro germination capacity of TH hybrid seed. Black lines represent F1_chimera, grey lines represent F1_TT.

Figure 14:
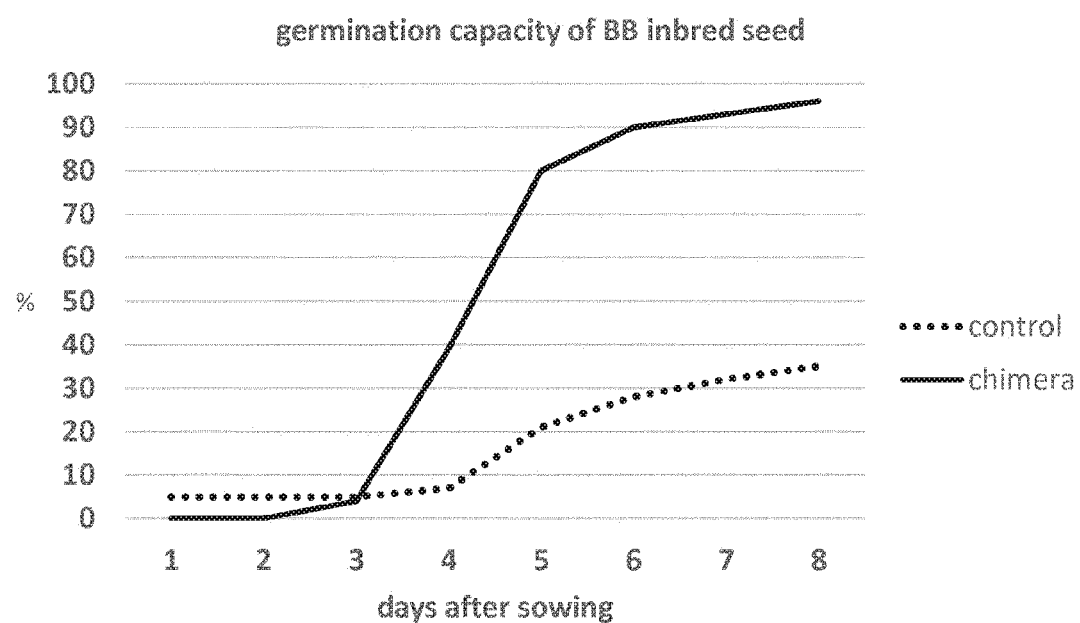

FIG. 14: In vitro germination capacity of BB seed produce by selfing a beef tomato plant (control) or a chimera comprising an L2 and L3 of beef tomato and L1 of F1 from cross Ailsa Craigs×cherry-type *S. lycopersicum* inbred line (chimera: black line).

Figure 15:
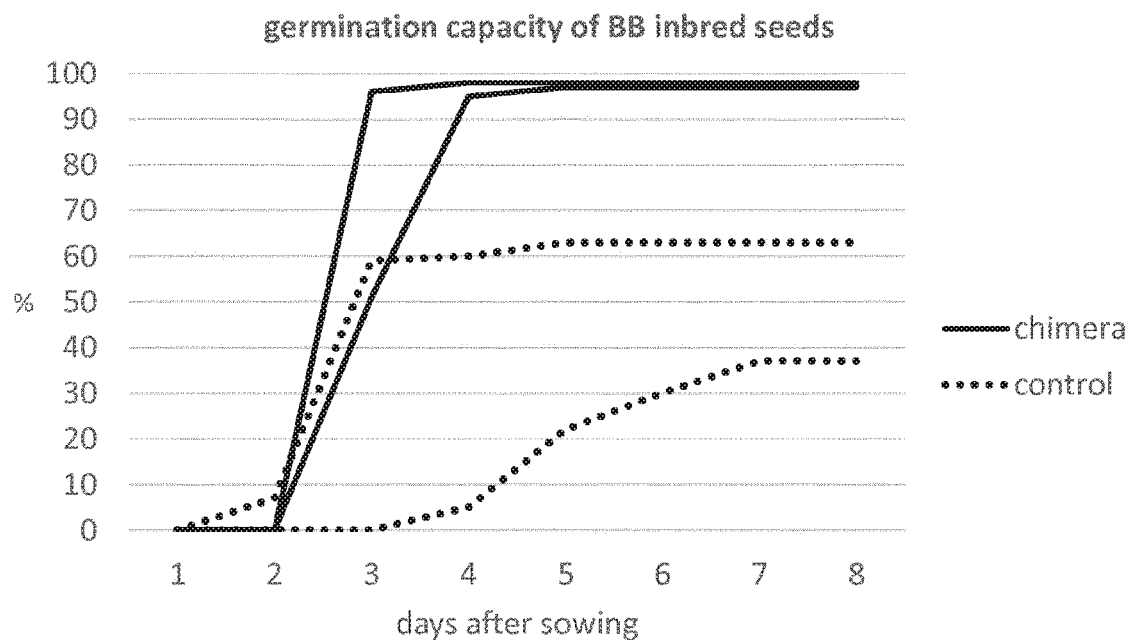

FIG. 15: In vitro germination capacity of BB seed produce by selfing a beef tomato plant (control) or a chimera comprising an L1 and L2 of beef tomato and L3 of F1 from cross Ailsa Craigs×cherry-type *S. lycopersicum* inbred line (chimera: black line).

Figure 16:
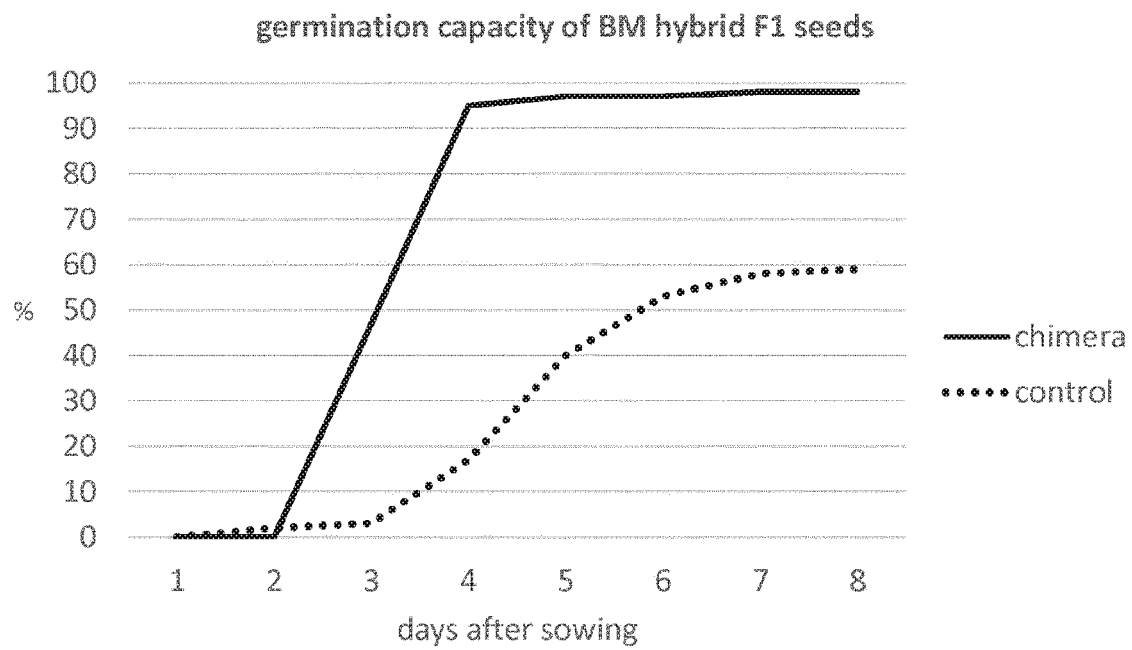

FIG. 16: In vitro germination capacity of BM seed. Black lines represent F1_chimera (chimera; progeny of the cross-fertilization of the chimera with line MM), grey lines represent F1_BB (control; progeny of the cross-fertilization of BB with line MM).

Figure 17:
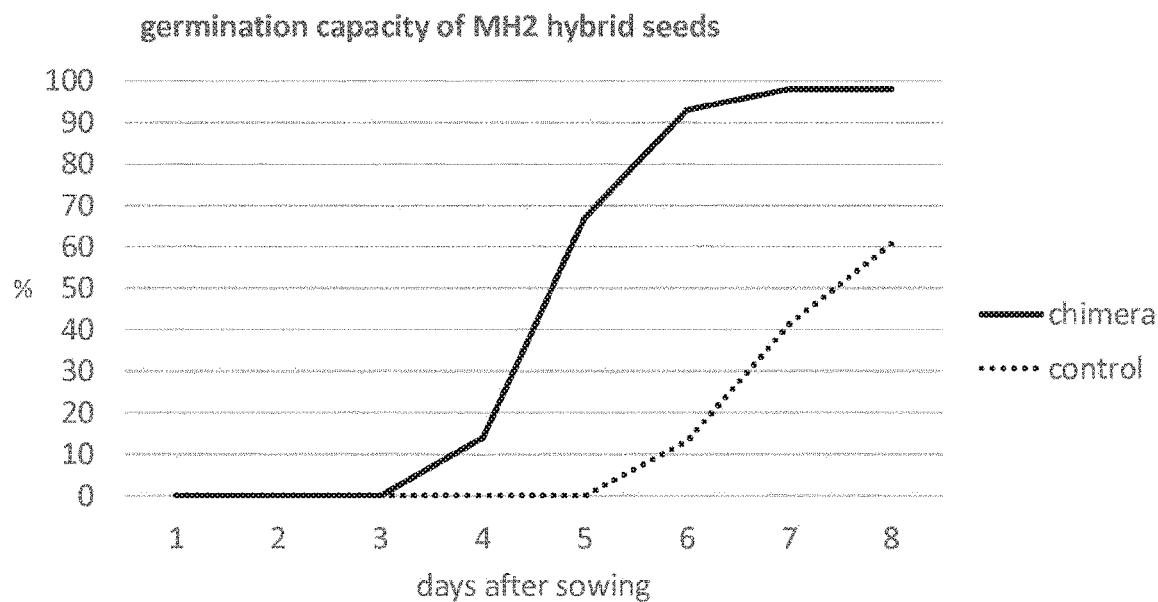

FIG. 17: In vitro germination capacity of MH2 seed. Black lines represent F1_chimera (chimera; progeny of the cross-fertilization of the chimera with line H2H2), grey lines represent F1_MM (control; progeny of the cross-fertilization of MM with line H2H2).

Figure 18:
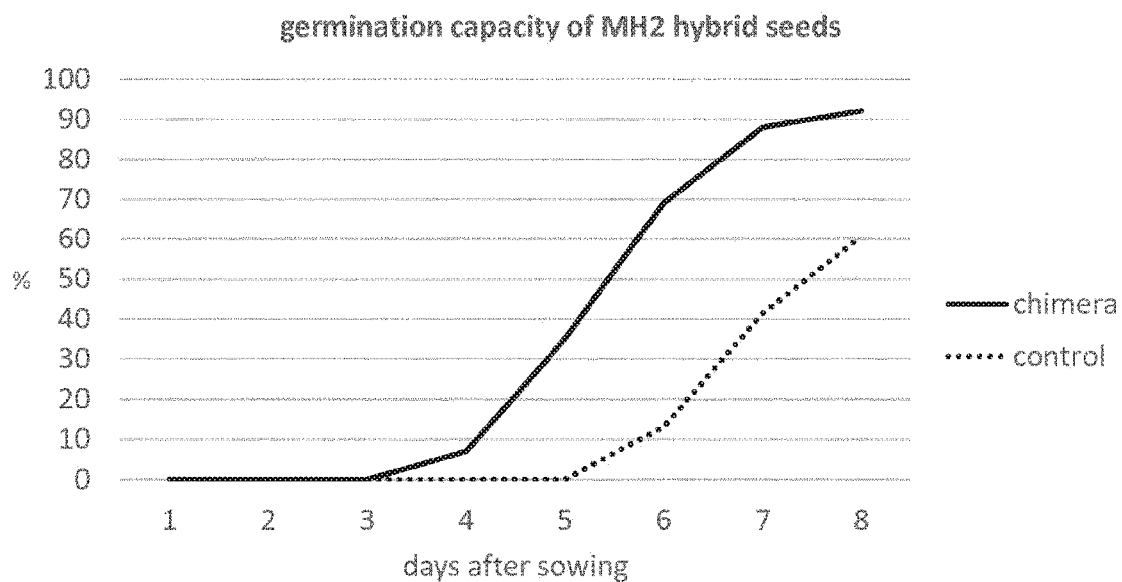

FIG. 18: In vitro germination capacity of MH2 seed. Black lines represent F1_chimera (chimera; progeny of the cross-fertilization of the chimera with line H2H2), grey lines represent F1_MM (control; progeny of the cross-fertilization of MM with line H2H2).

Figure 19:
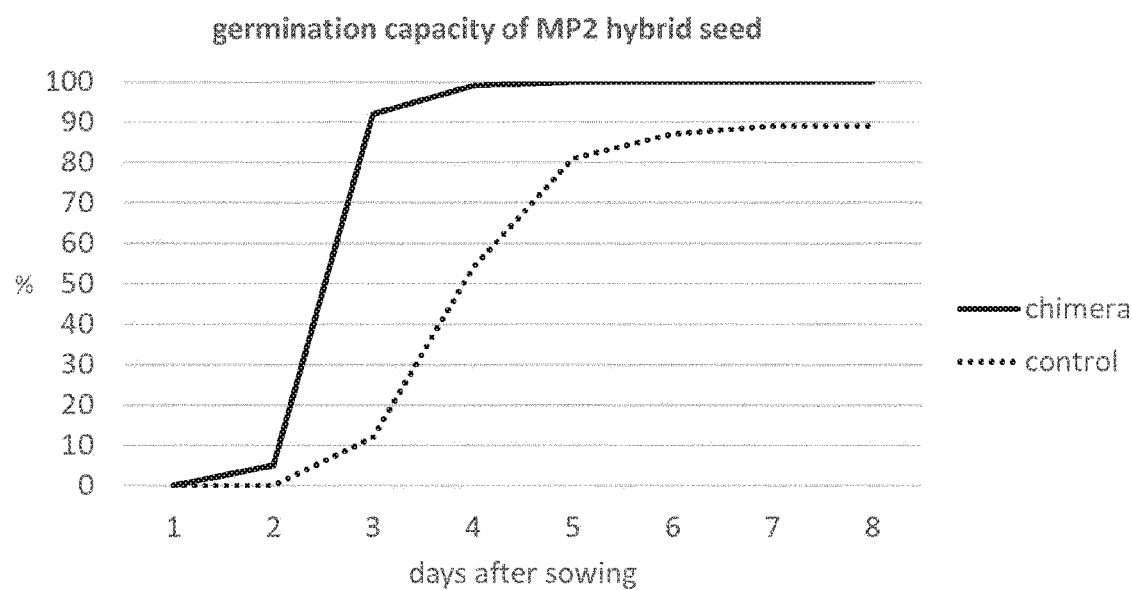

FIG. 19: In vitro germination capacity of MP2 seed. Black lines represent F1_chimera (chimera; progeny of the cross-fertilization of the chimera with line P2P2), grey lines represent F1_MM (control; progeny of the cross-fertilization of MM with line P2P2).

Figure 20:
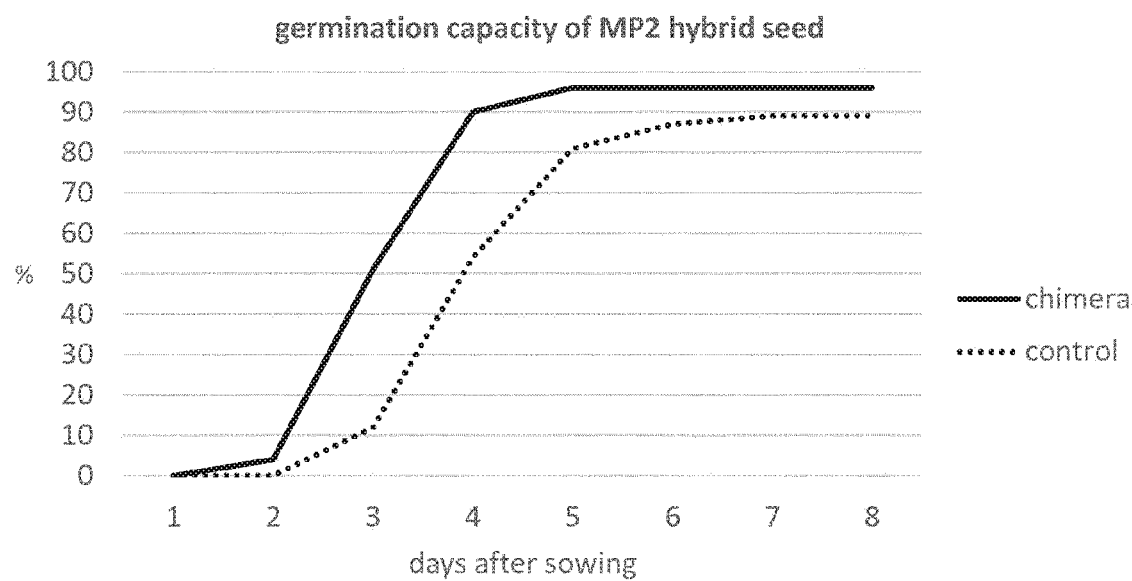

FIG. 20: In vitro germination capacity of MP2 seed. Black lines represent F1_chimera (chimera; progeny of the cross-fertilization of the chimera with line P2P2), grey lines represent F1_MM (control; progeny of the cross-fertilization of MM with line P2P2).

Figure 21:
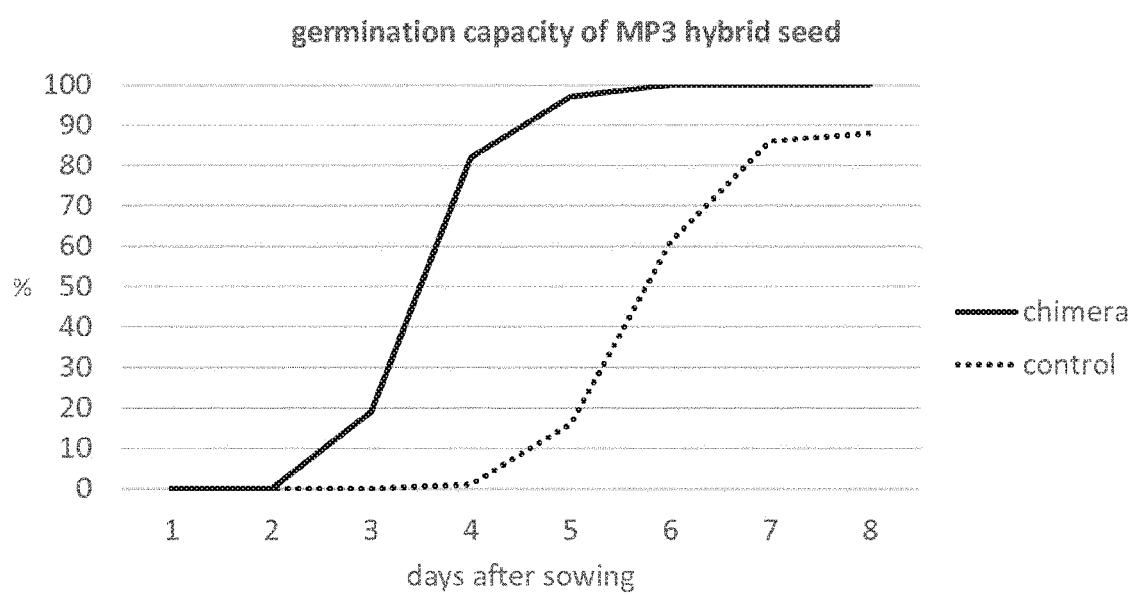

FIG. 21: In vitro germination capacity of MP3 seed. Black lines represent F1_chimera (chimera; progeny of the cross-fertilization of the chimera with line P3P3), grey lines represent F1_MM (control; progeny of the cross-fertilization of MM with line P3P3).

DESCRIPTION

Definitions

In the following description and examples, a number of terms is used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs.

As used herein, the terms "comprising" and "to comprise", and their conjugations, refer to a situation wherein said terms are used in their non-limiting sense to mean that items following the word are included, but items not specifically mentioned are not excluded. It also encompasses the more limiting verb "to consist of". In addition, reference to an element by the indefinite article "a" or "an" does not exclude the possibility that more than one of the element is present, unless the context clearly requires that there be one and only one of the elements. The indefinite article "a" or "an" thus usually means "at least one".

As used herein, the term "and/or" refers to a situation wherein one or more of the stated cases may occur, alone or in combination with at least one of the stated cases, up to with all of the stated cases.

Within the context of the present invention, germination of a seed means the first stage of the development of a plant from the seed embryo, in particular the emergence of the radicle from the seed coat.

Germination generally is facilitated by controlled pre-treatment of seeds with water during a process called priming. During priming, the seed undergoes hydration or partial hydration. After this priming process, seeds are usually dried again. After sowing or planting or otherwise distributing the seeds and exposure to water, the seeds will germinate.

Stratification is a process of pre-treating seeds in order to simulate the cold temperature conditions that seeds may have to endure before germination. Stratification is a way of breaking the embryonic dormancy phase. Usually a cold period, possibly combined with moist conditions, is applied in order to break the embryo's dormancy. Typically, but not limited to, temperatures applied are between 1-5° C. The period of treatment, temperature to be applied and moist conditioning depend on the plant species, and are known to the skilled person, or can be established by the skilled person. The period of time of stratification may for instance be between one week and 20 weeks, or between 1-3 months, depending on plant species and other environmental conditions of stratification. The seeds may be soaked in cold water, for instance between 2-20 hours depending on the plant species, before they are exposed to cold treatment. Also, in some cases the cold treatment is preceded by exposing the seeds to warm treatment, for instance at 12-25° C., depending on the plant species and for a period depending on the plant species. The skilled person knows how to choose the stratification conditions for a given plant species.

A seedling is a young plant developed out of a plant embryo present in a seed. A seedling comprises the radicle (embryonic root), the hypocotyl (embryonic stem), the cotyledons (embryonic leaves), the shoot apical meristem and the root apical meristem. Seedlings may, for instance, include the first true leaves in addition to the cotyledons. In such a case, the seedling may be referred to as a plantlet also.

The term genotype refers to the genetic makeup of a plant cell, a seedling, a plant part or a plant, including among other things the specific allele makeup of the plant cell, seedling, plant part or plant. As well-known by the skilled person, a constituent of a seed is the embryo. The term "embryo genotype" thus refers to the genetic makeup of this constituent of a seed. Genotyping refers to the process of determining genetic variations (e.g. SNPs) among subsets of for example different meristem layers or different (nonchimeric) plants.

Hybrid seed refers to seed produced from genetically different parents. Thus hybrid seed is genetically heterozygous, or mostly genetically heterozygous. Hybrid seed is also referred to as F1-hybrid seed.

Inbred seed is derived from an inbred line. An inbred line is a true-breeding line resulting from at least 1, 2, 3, 4, 5, 6, 7, 8, 9 or 10 successive generations of controlled self-fertilization, sibmating or backcrossing to a recurrent parent. Preferably, the inbred line is a true-breeding line resulting from at least 5 successive generations of controlled self-fertilization or backcrossing to a recurrent parent.

Similar environmental conditions means among other things the use of a similar temperature, humidity, nutrition and light conditions, and similar irrigation, day/night rhythm and fertilization regimes. These conditions are for instance the conditions under which the plants described herein are grown, including but not limited to non-chimeric plants with the genotype of the stem cells of the L3-shoot meristem layer of the periclinal chimera or non-chimeric plants with the genotype of the stem cells of the L1-shoot meristem layer of the periclinal chimera. Similar environmental conditions imply identical environmental conditions.

Partitioning of assimilates from the mother plant to the developing seeds relates to the relative level at which the mother provides resources, for example metabolites and/or hormones to the seed, the 'partitioning'.

Within the context of the present invention, the term seed germination properties refers to, among other things, to germination capacity, uniformity of germination, germination rate, seedling fresh weight and/or seed vigour.

Seed density relates to the specific weight of a seed. This density can be determined for instance by liquid density separation of seeds, for instance in sucrose gradients.

Figure 1:
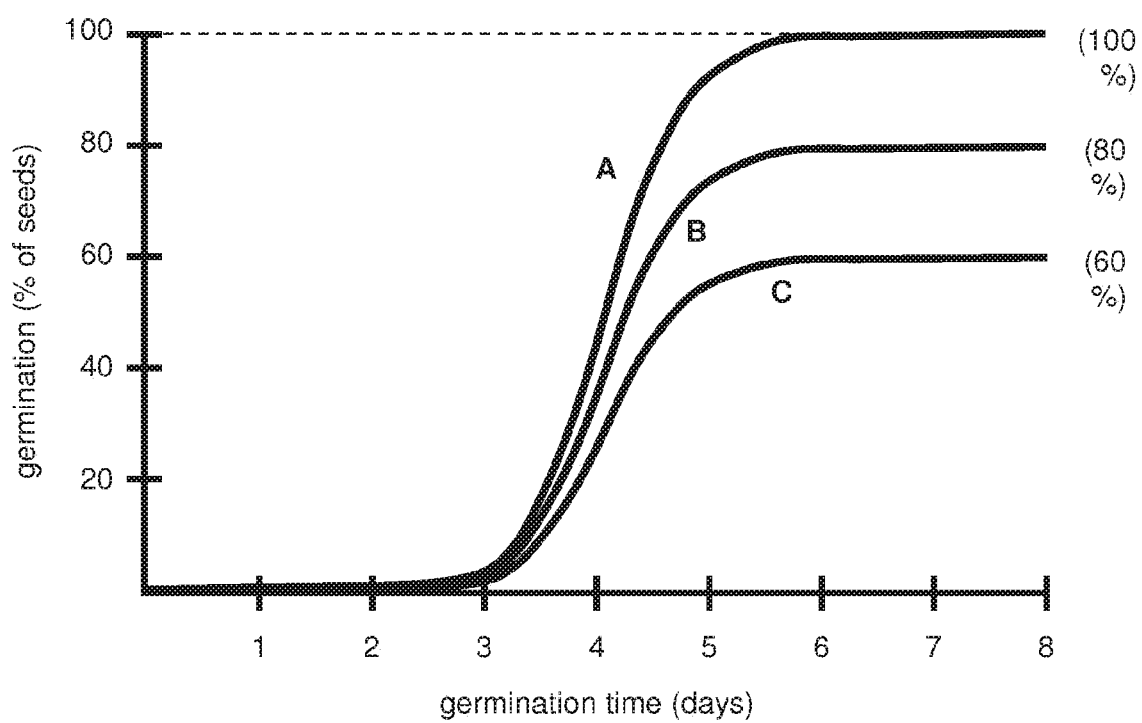
FIG. 1. Illustration of the development of the percentage of germinated seeds over time of plant lines with different germination capacity. Germination capacity is the number of germinated seeds expressed as a percentage of the total number of planted seeds in a given period of time. The period of time taken is long enough to make sure that the number of germinated seeds is levelling off in time, and reaches a plateau phase. This period of time for instance is 3 times the peak value time. This plateau phase may be 100%, when all seeds have germinated, or it may be a lower percentage, in case some seeds do not germinate at all. In the figure, line B is the control line with 80% germination capacity. Line A is an example of a line with improved germination capacity (100%), and line C an example of inferior germination capacity.

Within the context of the present invention, germination capacity means the percentage of sown or planted or otherwise distributed seeds that germinates, i.e. shows the emergence of the radicle, within a fixed period of time appropriate for the given plant species. Thus, germination capacity can be calculated as the number of seeds germinated divided by the total number of seeds sown or planted or otherwise distributed, recalculated as a percentage, within a given period of time. Seed germination properties may, for example be determined after sorting and selection procedures such as usual in agriculture and horticulture, and aimed at the specific plant species. Seeds may for example be separated by liquid density separation, or by X-ray sorting (for example as may be used for tomato seeds). The seeds may also be primed first. It is known to the skilled person how long the fixed period of time appropriate for a given plant species is. This period of time may for instance be 2, 3, 4 or 5 times the peak value time. Preferably it is 3 times the peak value time. It is known to the skilled person also that this period of time may vary according to environmental conditions. It is preferred that these conditions are optimal conditions for seed germination. The period of time is chosen thus long that variation in germination rate or germination uniformity does not influence the calculation of the germination capacity. The time period is appropriate if the skilled person can reasonably expect the majority of the seeds that are capable of germinating, to actually germinate within this time period. FIG. 1 illustrates the development of the percentage of germinated seeds over time of plant lines with different germination capacity. The period of time taken is long enough to make sure that the number of germinated seeds is levelling off in time, and reaches a plateau phase. This plateau phase may be 100%, when all seeds have germinated, or it may be a lower percentage, in case some seeds do not germinate at all. With germinating capacity is meant for instance 60%, 65%, 70%, 75%, 80%, 85%, 90% or 95%, depending on the plant species. Thus, an 85% germination capacity implies that 85% of the sown or planted or otherwise distributed seeds germinates, i.e. shows the emergence of a radicle, within a time period appropriate for the given plant species, for instance, but not limited to 3 times the peak value time. A higher germination capacity means that more seeds show emerged radicles. Examples of the fixed period of time appropriate for a given plant species in order to establish germination capacity under optimal environmental conditions are for instance, but not restricted to, about 5 days for *Arabidopsis*, about 7 days for barley, about 7 days for *Hypericum*, about 7 days for *Nicotiana*, about 7 days for tomato, about 28 days for buttercup, and about 30 days for *Impatiens*.

Within the context of the present invention, the peak value time is the period of time after sowing, planting or otherwise distributing seeds in order for them to germinate, possibly after sorting and selection of the seeds, or for example after priming and/or stratification of the seeds, on which the highest tangent is reached on the curve in which percentage of germinated seeds is plotted on the y-axis, and time on the x-axis. FIG. 2 illustrates the concept of peak value time. Thus the peak value time is determined as the period of time required to reach the moment on which the increase in the number of germinating seeds per unit of time is the highest. The peak value time can be used to assist in calculating germination capacity or germination rate, for instance by fixing a time period of 2, 3, 4 or 5 times the peak value time, preferably 3 times the peak value time.

Within the context of the present invention, uniformity of seed germination or germination uniformity is the time (T) required to reach a fixed percentage of germinated seeds (X). This fixed percentage maybe 50% (T50), 75% (T75), 80% (T80), 90% (T90), 95% (T95), 99% (T99) or any percentage appropriate for a particular seed batch. The shorter this time, the higher the uniformity. It is known to the skilled person that uniformity of seed germination may vary according to environmental conditions. It is preferred that these conditions are optimal conditions for seed germination. Uniformity of seed germination is measured in such a way that it is in principle, but not necessarily, independent of germination capacity or germination rate.

Within the context of the present invention, germination rate is defined as the weighted sum of total germinated seeds per day. In formula form: rate=(number of germinated seeds on day 1, divided by 1)+(number of germinated seeds on day 2, divided by 2)++(number of germinated seeds on day Z, divided by Z) wherein Z is the last day of measurement. This measure is the same as the Germination Index (GI) defined by the American Association of Seed Analysts (AOSA) (AOSA, 1983. Seed vigor testing handbook. Contribution No. 32 to handbook on seed testing. Association of Official Seed Analysts). The germination rate is determined over a time period that is appropriate for the given plant species, and is the time period in which the skilled person can reasonably expect the majority of the seeds that are capable of germinating to actually germinate. The skilled person knows how to determine this time period. This period of time may for instance be 2, 3, 4 or 5 times the peak value time. Preferably it is 3 times the peak value time. It is known to the skilled person that germination rate may vary according to environmental conditions. It is preferred that these conditions are optimal conditions for seed germination. However, improved quality of a seed batch may also be assessed as a germination rate that is enhanced under suboptimal conditions, which may be prevalent in agronomic or horticultural practice.

Within the context of the present invention, seed vigour means the ability of the seedling emerging from the seed to survive and grow when planted. Thus, seeds have a higher vigour, if under similar conditions a higher percentage of seedlings survives, and grows into seedlings or plantlets with emerged first true leaves, first by expanding the cotyledons, then by enlarging the shoot, and finally by producing the first true leaves. If under the same conditions a higher percentage of seedlings or plantlets with the first true leaves emerged can be observed within a certain time period which depends on the plant species, the seed vigour is considered higher. Seed vigour is also considered higher if the total biomass (fresh weight and/or dry weight) of the seedlings is larger after a fixed time period after sowing. Thus, seedling fresh weight is among other things a measure of seed vigour.

Within the context of the present invention, seed phenotypic properties are defined as the biochemical and biophysical aspects of seed composition that are determined by the maternal tissues of the plant, and not by the filial tissues (embryo and endosperm). Phenotypical properties may be the amount and chemical composition of storage reserves within embryo and endosperm as determined by supplies of primary nutrients (carbohydrates, minerals, etc.) by the maternal tissues of the plant. Other phenotypical properties may be the rigidity and/or thickness of the maternally derived seed coat. The term phenotypic properties encompasses physiological properties. Seed phenotypic properties relate to seed germination properties.

Altered or altering within the context of the present invention means that a seed derived from crossing a plant A with a plant B is compared for its phenotypical or physiological properties, more in particular its germination properties, to a seed obtained from a periclinal chimera plant according to the present invention, and said phenotypical and/or physiological properties are changed, preferably are improved. A periclinal chimera plant according to the present invention is a plant comprising an L2-shoot meristem layer that has the genotype of plant A, whereas the L1 and/or L3-shoot meristem layer has a different genotype. A non-chimeric plant according to the present invention is a plant comprising an L2-shoot meristem layer that has the same genotype as its L1 and L3-shoot meristem layer. A seed obtained from the periclinal plant according to the present invention may exhibit an enhanced germination rate, germination capacity and/or seedling fresh weight compared to a seed derived from a cross of plant A with plant B. A seed obtained or obtainable from a method of the present invention may exhibit at least one of an altered or improved seed density distribution, enhanced germination rate, enhanced germination capacity, improved germination uniformity, improved seed vigour, and seedling fresh weight compared to a seed derived from a cross of plant A with plant B, when tested under the similar environmental conditions. Plants A and B may have an identical genotype, in which case the seed obtained is inbred seed, or they may have different genotypes, in which case the seed obtained is hybrid seed.

Although the definitions provided are complete and sufficient, in the possible absence of directions, further definitions as provided in that art can be found in the handbook of the International Seed Testing Association (ISTA), and on websites of the seed trade, such as http://www.fao.org/docrep/006/ad232e/ad232e09.htm or http://www.seedbiology.de/germination.asp. Definitions according to these sources can be consulted in so far as they do not contradict the definitions given above; in case of a contradiction, the definitions provided above apply.

DETAILED DESCRIPTION

The invention provides for a method of producing a periclinal chimera plant suitable for producing seed having seed with an embryo genotype identical to seed obtained by crossing a first plant A with a second plant B, wherein one or more germination properties of the seed are altered and/or improved, wherein the method comprises the steps of:
 i) provision of a first plant A and a third plant C; and
 ii) making a periclinal chimera plant comprising an L2-shoot meristem layer that has the genotype of plant A, and an L1 and/or L3 shoot meristem layer that has the genotype of a third plant C.

Preferably, the produced periclinal chimera is suitable for pollination with pollen of second plant B.

The invention also provides for a method for producing said seed using said periclinal chimera plant as a mother plant. Hence, the invention also provides for a method for producing and/or altering the germination properties of a seed, but without the need to influence the genotype of the embryo of the seed. Said method comprises the steps of:
 a) making a periclinal chimera plant comprising an L2-shoot meristem layer that has the genotype of plant A, and an L1- and/or L3-shoot meristem layer that has the genotype of a third plant C;
 b) pollinating the periclinal chimera plant with pollen of plant B;
 c) harvesting the seed thus obtained;
wherein the seed embryo has a genotype that is identical to seed obtained by crossing a first plant A with a second plant B.

As earlier indicated herein, a first plant A (also denominated herein as "plant A") and a third plant C (also denominate herein as "plant C") are to be understood herein as non-chimeric plants, i.e. having the same genotype for all three meristem layers L1, L2 and L3. The second plant B (also denominated herein as "plant B"), may be a chimeric or a non-chimeric plant. In cases wherein plant B is a chimeric plant, "the genotype of plant B" is to be construed herein as "the genotype of the L2-layer of plant B". Crossing a first plant A with a second plant B is to be understood herein as crossing a first plant A as female plant with a second plant B as male plant. L1- and/or L3-shoot meristem layer is to be understood as any one of L1-shoot meristem layer, L3-shoot meristem layer and both L1- and L3-shoot meristem layer. At least one or more germination property of the seed harvested in step c may be altered, preferably improved, as compared to seed that is obtained by crossing plant A with plant B, when tested under similar environmental conditions. Preferably, the one or more germination properties are significantly enhanced as compared to seed that is obtained by crossing plant A with plant B, when tested under similar environmental conditions. Preferably, the at least one germination property is any one of germination capacity, germination uniformity, germination rate, seed density, seedling fresh weight and/or seed vigour. Optionally at least 2, 3, 4, 5 or 6 germination properties are improved or enhanced. Preferably, the seed obtained in step c shows enhanced germination capacity and enhanced germination rate; enhanced germination capacity and enhanced seedling fresh weight; enhanced germination rate and enhanced seedling fresh weight; or enhanced enhanced germination capacity, enhanced germination rate and enhanced seedling fresh weight, as compared to seed obtained from crossing plant A with plant B (by pollinating plant A with pollen of plant B), when tested under similar environmental conditions. The method may further comprise a step of assessing at least one germination property of the seed obtained in step c and/or allowing the seed obtained in step c to germinate. Therefore, also provided is a method for assessing at least one germination property of such seed, which comprises the above defined steps a-c and a subsequent step for assessing at least one germination property of seed obtained. Preferably, the at least one germination property is any one of germination capacity, germination uniformity, germination rate, seed density, seedling fresh weight and/or seed vigour. Optionally at least 2, 3, 4, 5 or 6 germination properties are assessed. Preferably, these germination properties are compared to the germination properties of seed obtained by crossing a first non-chimeric plant A (as female plant) with a second plant B (as male plant). Optionally, this method further comprises a step of germinating the seed before assessing at least one germination property. Further provided is a method for germinating seed, said method comprises the steps a-c defined above and a subsequent step d) allowing the seed obtained in step c to germinate. Optionally, this method further comprises a subsequent step of assessing at least one germination property. The invention also provides for the use of a periclinal chimera plant in any one of these methods.

In a preferred embodiment, the genotype of the endosperm is not influenced either. For example, with the invention there may be provided for seed with altered (e.g.

improved) seed density, biomass, germination rate, germination capacity, seed vigour fresh and/or weight of seedlings. Preferably, the germination rate, germination capacity and/or seedling fresh weight are enhanced as compared to seed obtained by crossing a first plant A (as female plant) with a second plant B (as male plant).

The germination properties of a seed with an embryo genotype that is obtained by crossing a first plant A with a second plant B can be altered or improved without altering the genetic make-up of the offspring of a cross of plant A or B. This goal is achieved by a method wherein a periclinal chimera is prepared that comprises a L1 and/or L3 layer from a third plant C and a L2 layer from the first plant A and crossing thereof, for instance by pollination, with the second plant B. The seed thus obtained from the chimera shows an embryo genotype that is identical to the embryo genotype of the seeds obtained by crossing the first plant A and the second plant B, but displays modified germination properties in comparison to seeds obtained by crossing the first plant A and the second plant B. The problem solved is modification of germination properties of a seed without modifying the embryo genotype of the seed. The solution is using a chimera constructed as mentioned above. The germination properties to be modified may for example be related to seed density, biomass, germination rate, germination capacity and/or fresh weight of seedling, but may also be any other desired change in germination property.

The third plant C, used in the chimera, may be selected based on the germination property modification desired, and in particular in view of those related to the quality of the seed. For example, plant C may be a plant known to produce seeds with a given density, biomass, or known to provide seeds with a given germination capacity or fresh weight of seedling. Such plant C may than be used in the chimera in order to modify the germination properties of the seed to more resemble the germination properties of that of plant C. For instance, for many purposes in tomato seed production use of tomato variety Ailsa Craig as plant C may prove advantageous. Selection of plant C may also, or in addition to the selection criteria cited above, be based on the presence and/or germination properties of seed obtained from a cross of plant C with plant B. In other words, in case it is known or established that a cross of plant C and plant B results in seed, preferably said seed having acceptable or good germination properties, the genotype of plant C may be selected as the genotype for the L1 and/or L3 layer of the periclinal chimera plant used in the method of the present invention. In dicots, tissues of plants derive from pluripotent stem cells in three clonally distinct cell layers of the shoot apical meristems, namely the L1, L2 and L3 clonal cell layers. The L1 clonal cell layer makes the epidermis. The L3 clonal cell layer gives rise to a major portion of internal tissues in all plant organs, including the vascular transport system i.e. xylem and phloem, and controls the number of ovules in the ovary of a fruit, and the accumulation of assimilates in the seeds, and hence seed germination property and quality. Also the L1 clonal cell layer contributes to seed quality, as it gives rise to the integuments of the ovule which develop into the seed coat or testa, and which are involved in food supply. The female gametophytes and hence the egg cells, in contrast, are derived separately and exclusively from the L2 clonal cell layer. Thus, the cells and tissues derived from the respective stem cells in the three cell layers of the shoot apical meristem have the respective genotypes of these stem cells in the three cell layers of the shoot apical meristems.

"Periclinal chimeras" are chimeras in which one or more entire cell layer(s) L1, L2, and/or L3 is genetically distinct from another cell layer. In the case of periclinal chimeras, a single tissue layer itself is homogeneous and not chimeric. Periclinal chimeras are the most stable form of chimeras, and produce distinctive and valuable plant phenotypes. These plants produce axillary buds that possess the same apical organization as the terminal meristem from which they were generated. Therefore, periclinal chimeras can be multiplied by vegetative propagation and maintain their chimera layer organization. Periclinal chimeras can be made by somatic mutagenesis of stem cells in one of the (L1-, L2-, L3-) layers of the shoot meristem. Periclinal chimeras can also be produced by synthetic methods, for example as described by Szymkowiak, E. J., and Sussex, I. M. (1992), The internal meristem layer (L3) determines floral meristem size and carpel number in tomato periclinal chimeras, Plant Cell 4, 1089-1100. Said periclinal chimeras are an example of interspecific cell layer transplantations occurring between the two grafted species. This particular method is practiced under ambient conditions, in a growth room or greenhouse. It consists of regular grafting of two plants, one as rootstock and another as scion. Graft unions, after healing, are cut and allowed to regenerate adventitious shoots. Among these adventitious shoots, chimeras can appear spontaneously. In vitro synthetic techniques have also been developed to produce periclinal chimeras. These include: (1) co-culturing of cells, wherein adjoined stem slices from two different plants are cultured together into chimeral callus, and adventitious chimeric shoots are regenerated from these calli on hormone-supplemented in vitro growth media. (2) mixed callus cultures, wherein cell-suspensions of two different plants are mixed, the mixtures are grown into chimeral callus, and adventitious chimeric shoots are regenerated from these calli on hormone-supplemented in vitro growth media. (3) co-culture of protoplasts, wherein protoplast suspensions of two different plants are embedded in agarose and grown to very high cell densities, upon which chimeric shoot are regenerated on hormone-supplemented in vitro growth media. (4) in vitro graft culture, wherein two seedlings are grafted along their hypocotyls under sterile conditions, and sub-apical cross sections of the grafts are cultured to induce chimeric adventitious calli and shoots. Such techniques fall under the common denominator of tissue culture, and consist of a multitude of distinct protocols that may be specific for individual plant lines or species. The skilled person will know how to bring cells of two different plants together in tissue culture, to regenerate plants which may or may not be periclinal chimeras. For an elaborate review on plant chimeras, see "Plant Chimeras" by Richard A. E. Tilney-Bassett (Cambridge University Press, 1991).

The present invention provides a method of producing periclinal chimeras. These periclinal chimeras enable the production of seeds of a certain desired genotype, determined by the genotype of the L2 clonal cell layer as well as the genotype of the pollen. The seeds are grown on such a periclinal chimera plant with an L3 clonal cell layer that has a different genotype than the L2 clonal cell layer and/or with a L1-clonal cell layer that has a different genotype as the L2 clonal cell layer. The choice of the genotype of the L3 clonal cell layer and/or the L1-clonal layer can be made in such a way that it is selected for the maternal properties (of the plant from which it is derived), such as ovule properties, fruit size, vegetative vigour and good nurturing of developing seeds. In other aspects it may be an inferior line. However, it is preferred that the choice of the genotype of the L3 and/or the L1 clonal cell layer is such that the L3 and/or L1 layer may independently or combined contribute to altered (e.g. improved) germination properties of the seed produced, and the production of better quality seeds (e.g. seeds with improved germination properties such as enhanced germination rate, germination capacity and/or seedling fresh weight) with the method according to the invention.

Since the L3 and/or L1 clonal cell layer does not contribute genetically to the offspring, but functions only to provide the seeds with resources and to determine germination properties and quality of seeds, the choice of the genotype of the L3 and/or L1 clonal layer of the plant will allow for the production of seeds with altered (e.g. improved) germination properties and a higher quality than would be determined by the non-chimeric plant consisting of L2 genotype only. In other words, compared to seed produced by a non-chimeric plant consisting of L2 genotype only, the seed produced by the periclinal chimera plant of the invention shows altered (e.g. improved) germination properties, in particular improved germination properties such as enhanced germination rate, germination capacity and/or seedling fresh weight.

In one embodiment, upon crossing with a male plant (plant B) with the same genotype as the L2 clonal cell layer, the resulting gametes of such a periclinal chimera are genotypically determined by the L2 clonal cell layer, but the amount of assimilates directed to the seeds are determined by the genotype of the L1 and/or L3 clonal cell layer, and yet other seed properties such as seed coat thickness are determined by the genotype of the L1 clonal cell layer.

In a preferred embodiment, the L1 and/or L3-clonal layer is selected such that a non-chimeric plant with the genotype of the stem cells of the L1 and/or L3-shoot meristem is female-sterile. Sporadically, L1 and L3 cells may invade the L2 layer, leading to a percentage of undesired impurity in seeds obtained with the methods according to the invention. With the provision of a L1 and/or L3-clonal layer such that a non-chimeric plant with the genotype of the stem cells of the L1 and/or L3-shoot meristem is female-sterile this undesired impurity is prevented. All forms of female sterility can be used for this purpose, for example the sterility may be genetic, e.g. through the use of mutations involved in the development and function of (parts of) the female gametophyte. Alternatively, it may be cytogenetic, using polyploids or aneuploids to create inviable eggs, inviable endosperm, or inviable embryos when crossed with e.g. diploid or euploid pollen donor plants.

For example, in an inbred line A of tomato, a maximum intrinsic germination capacity, of 60% is observed. To improve this capacity, a periclinal chimera is produced with the L2 layer of line A, and with the L1 layer and the L3 layer of a line C of tomato. Line C is chosen for its intrinsically high germination capacity of 95%. A periclinal chimera is made by grafting seedlings of lines A and C, consisting of the steps of (1) transversely cutting and then adjoining and reunion of their hypocotyls, (2) cutting transversely through the graft junction, and (3) letting callus develop and adventious shoots regenerate from the site of the graft union and (4) selecting chimeras among the regenerated plants. Techniques for steps 1-4 are known to a person skilled in the art. Generally, using grafting and regeneration, the frequency with which periclinal chimeras emerge among the adventitious shoots will be ~0.2%-10%. Therefore, a large number of seedlings of lines A and C is grafted, and many independent adventitious shoots are generated. Each of these adventitious shoots is grown into plantlets of around 5 cm in length, carrying a few leaves. From these plantlets, the apical shoot tip is removed to allow axillary shoots to emerge from the leaf axils. Periclinal chimeras are identified among these axillary shoots, by the use of genetic markers that distinguish the constituent lines A and C. These markers may be phenotypic, for example a distinctive leaf colour, or any morphological or biochemical difference, such as fruit shape. These markers may also be genotypic, such as a DNA or RNA sequence polymorphism between lines A and C. Phenotypic and/or genotypic markers are detected by an appropriate detection method and applied to all axillary shoots from all adventious shoots regenerated from all individual grafted plant-pairs. Periclinal chimeras are recognized as having markers of both lines A and C combined in a single plant, as a result of adventitious shoot regeneration from graft juntions and not of sexual hybridization. Such chimeras stably retain these markers during further growth of the plant, including their axillary shoots, inflorescences, flowers, and all other aerial parts of the plants that arise from natural growth and development from the periclinal chimeric shoot apical meristem. Periclinal chimeras of the desired type, in terms of the constitution of its stem cell layers L(1,2,3), are identified by observing the presence of the markers in specific tissues, e.g. in the epidermis (L1), the vasculature (L3), the pollen grains (L2), or any other tissue known to mainly derive from these layers. The germination capacity of pure line A seed is now improved by pollinating the periclinal chimera of type (L1(C); L2(A); L3(C)) with pollen of the genotype of line A. This pollen is taken from non-chimeric line A plants, or from the chimera itself in which case the periclinal chimera is self-fertilized. The seeds harvested from such pollinations are of pure genotype A, because maternal and paternal gametophytes are exclusively derived from the L2 layer. The altered (e.g. improved) germination property and improved germination capacity of line A seed lots, obtained in this way, is assessed by regular sowing experiments. Line A seed lots of premium quality are produced in this way, and these can be processed according to standard procedures, and can subsequently be made available for (commercial) distribution.

The present invention also provides a method of producing F1-hybrid seed, wherein the periclinal chimera as described above is crossed with a male plant of a desired genotype in order to produce F1-hybrid seed consisting of the genotypes of the L2 clonal cell layer of the periclinal chimera as well as the genotype of the male plant.

Preferably, the method of the invention as defined herein, i.e. the method of producing seed and/or of altering the germination properties of seed, includes a further step, a step of assessing at least one germination property of the seed obtained. Germination properties can be assessed by regular sowing experiments. The method of the invention may comprise the identification and/or selection of seed showing altered, preferably improved, germination properties as defined herein above, wherein altered or improved is to be understood as altered or improved as compared to the germination properties of the seed resulting from a cross of plant A with plant B, when tested under similar environmental conditions.

In a method or use of the invention, the genotypes of plants A and C may differ from each other. In case the periclinal chimera within the method or use of the invention comprises an L1 having genotype of plant C, the L3-layer of the chimera preferably has the genotype of plant A or C. In case the periclinal chimera within the method or use of the invention comprises an L3 having genotype of plant C, the L1-layer of the chimera preferably has the genotype of plant A or C. Both the L1 and L3-shoot meristem layer of the periclinal chimera plant may have the genotype of plant C. Optionally, in the periclinal chimera plant the genotype of plant C comprises part of the genotype of plant A and/or plant B. In an embodiment, plant C can be a hybrid and/or inbred plant obtained from a cross of plant A and plant B (including optional selfing-, sibmating- and/or back-cross steps), comprising part of the genotype of plant A and/or plant B. For instance, the genotypic contribution of plant A to the total genotype of plant C is at least 0.5%, preferably at least 2%, more preferably at least 5%, even more preferably at least 10%, yet even more preferably at least 20%, most preferably at least 30% or at least 50%. In addition or alternatively, the genotypic contribution of plant B to the total genotype of plant C within this embodiment is at least 0.5%, preferably at least 2%, more preferably at least 5%, even more preferably at least 10%, yet even more preferably at least 20%, most preferably at least 30% or at least 50%. In other words, optionally the L1 and/or L3-shoot meristem layer of the periclinal chimera plant comprises part of the genotype of plant A and/or plant B. The genotype of the L1-shoot meristem layer in the periclinal chimera plant may comprise part of the genotype of plant B, preferably of L2-shoot meristem layer of plant B. The genotype of plant A may be identical to or may be different from the genotype of plant B, preferably identical or different from the L2-shoot meristem layer of plant B. In other words, the genotype of the L2-shoot meristem layer of the periclinal chimera plant may be identical or may be different from the genotype of plant B, preferably the L2-shoot meristem layer of plant B, used for pollinating the periclinal chimera plant in step b defined above. Optionally, in step b defined above the periclinal chimera plant is self-fertilized. Plant B of the method or use of the invention may be a non-chimeric plant. The first plant A and the third plant C of the method or use of the invention may belong to species of the same genus and/or hybrids or inbred of species of said genus. The first plant A, the second plant B, and the third plant C of the method or use of the invention may be all from species of the same genus and/or hybrids or inbred of species of said genus. Optionally, the third plant C may produce seed with enhanced one or more germination properties, such as germination rate, germination capacity and/or seedling fresh weight, compared to seed produced by said first plant A. In a method or use of the invention, seed of a rootstock variety may be produced. The method or use may be for the production of tomato seed. One or more plants or hybrid or inbred plants A, B and C of the method or use of the invention may be from species belonging to the genus *Solanum*. One or more plants or hybrid or inbred plants A, B and C of the method or use of the invention may be selected from the group of species of *Solanum lycopersicum, Solanum pennellii, Solanum habrochaites* and *Solanum pimpinellifolium* or hybrids or inbreds thereof. Optionally, plant C may be a first generation F1 hybrid plant, preferably a *Solanum lycopersicum×Solanum pennellii* F1 hybrid plant, a *Solanum lycopersicum×Solanum habrochaites* F1 hybrid plant or a *Solanum lycopersicum×Solanum pimpinellifolium* F1 hybrid plant. Optionally, plant C is a hybrid or inbred plant, preferably a *Solanum lycopersicum×Solanum pennellii* hybrid or inbred plant, a *Solanum lycopersicum×Solanum habrochaites* hybrid or inbred plant or a *Solanum lycopersicum×Solanum pimpinellifolium* hybrid or inbred plant, wherein the genotypic contribution of each species to the total genotype is at least 0.5%, preferably at least 2%, more preferably at least 5%, even more preferably at least 10%, yet even more preferably at least 20%, most preferably at least 30% or at least 50%. At least 50% of the genotype of plant C may be the genotype of tomato variety Ailsa Craig. The L1- and/or L3-shoot meristem layer of the periclinal chimera plant of the method or use of the invention may have the genotype of a *Solanum lycopersicum* variety Ailsa Craig×*Solanum pennellii* hybrid plant, a *Solanum lycopersicum* variety Ailsa Craig×*Solanum habrochaites* hybrid plant or a *Solanum lycopersicum* variety Ailsa Craig×*Solanum pimpinellifolium* hybrid plant.

Preferably, at least one of plant A, B and C is a *Solanum lycopersicum* plant. Preferably the *S. lycopersicum* plant is a *Solanum lycopersicum* plant variety Ailsa Craig. Preferably the *Solanum lycopersicum* plant variety Ailsa Craig can have accession number LA3579. Preferably the *S. lycopersicum* plant is a *Solanum lycopersicum* beef variety (e.g. having more than 2, preferably more than 3 locules). Preferably the *Solanum lycopersicum* plant is a MoneyMaker variety. Preferably the MoneyMaker variety can have accession LA2706. Preferably, the *S. lycopersicum* plant is a cherry-type *S. lycopersicum* plant. Preferably, a *Solanum lycopersicum* var. *cerasiforme*.

Preferably, at least one of plant A, B and C is a *Solanum pennellii* plant. Preferably, the *Solanum pennellii* plant is a *S. pennellii* accession LA716.

Preferably, at least one of plant A, B and C is a *S. habrochaites* plant. Preferably, the *S. habrochaites* plant is a *S. habrochaites* accession P1127826.

Preferably, at least one of plant A, plant B and plant C is not *Solanum nigrum*. Preferably, Plant A, plant B and plant C is not *Solanum nigrum*.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum pennellii* line; plant C and L1-shoot meristem layer of the periclinal chimera plant have the genotype of a first generation F1 hybrid of an *Solanum lycopersicum* inbred line with *Solanum pennellii*; and the L3-shoot meristem layer preferably has the genotype of the L1- or L2-shoot meristem layer. All other variables may be as defined herein above. Preferably, within this embodiment, plant B is a plant of *Solanum pennellii* line LA716 and plant C and L1-shoot meristem layer of the periclinal chimera plant have the genotype of a first generation F1 hybrid of the *Solanum lycopersicum* inbred line Ailsa Craig with *Solanum pennellii* line LA716.

In a further embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum pennellii* line; plant C and the L3- and shoot meristem layer of the periclinal chimera plant have the genotype of a first generation F1 hybrid of an *Solanum lycopersicum* inbred line with *Solanum pennellii*; and the L1-shoot meristem layer preferably has the genotype of the L2- or L3-shoot meristem layer. All other variables may be as defined herein above. Preferably, within this embodiment, plant B is a plant of *Solanum pennellii* line LA716 and plant C and L1-shoot meristem layer of the periclinal chimera plant have the genotype of a first generation F1 hybrid of the *Solanum lycopersicum* inbred line Ailsa Craig with *Solanum pennellii* line LA716.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum habrochaites* line; plant C and L1-shoot meristem layer of the periclinal chimera plant have the genotype of a first generation F1 hybrid of an *Solanum lycopersicum* inbred line with *Solanum pennellii*; and the L3-shoot meristem layer preferably has the genotype of the L1- or L2-shoot meristem layer. All other variables may be as defined herein above. Preferably, within this embodiment plant B is a plant of *Solanum habrochaites* accession number PI127826 and plant C and L1-shoot meristem layer of the periclinal chimera plant have the genotype of a first generation F1 hybrid of the *Solanum lycopersicum* inbred line Ailsa Craig with *Solanum pennellii* line LA716.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum habrochaites* line; plant C and L3-shoot meristem layer of the periclinal chimera plant have the genotype of a first generation F1 hybrid of an *Solanum lycopersicum* inbred line, with *Solanum pennellii*; and the L1-shoot meristem layer preferably has the genotype of the L2- or L3-shoot meristem layer. All other variables may be as defined herein above. Preferably, within this embodiment plant B is a plant of *Solanum habrochaites* accession number PI127826 and plant C and L1-shoot meristem layer of the periclinal chimera plant have the genotype of a first generation F1 hybrid of the *Solanum lycopersicum* inbred line Ailsa Craig with *Solanum pennellii* line LA716.

In an embodiment of the method or use of the invention, plant A and the L2-shoot meristem layer of the periclinal chimera plant have the genotype of an inbred line of a beef variety of *Solanum lycopersicum*; plant B, more in particular the L2-shoot meristem layer of plant B also has the genotype of an inbred line of a beef variety of *Solanum lycopersicum*; plant C and L1-shoot meristem layer of the periclinal chimera plant have the genotype of a first generation F1 hybrid of a *S. lycopersicum* inbred line and a cherry-type *S. lycopersicum* inbred line; and the L3-shoot meristem layer preferably has the genotype of the L1- or L2-shoot meristem layer, preferably the L2-shoot meristem layer. All other variables may be as defined herein above. Preferably, within this embodiment plant C and L1-shoot meristem layer of the periclinal chimera plant have the genotype of a first generation F1 hybrid of the *Solanum lycopersicum* inbred line Ailsa Craig with the cherry-type *S. lycopersicum* inbred line.

In an embodiment of the method or use of the invention, plant A and the L2-shoot meristem layer of the periclinal chimera plant have the genotype of an inbred line of a beef variety of *Solanum lycopersicum*; plant B, more in particular the L2-shoot meristem layer of plant B also has the genotype of an inbred line of a beef variety of *Solanum lycopersicum*; plant C and L3-shoot meristem layer of the periclinal chimera plant have the genotype of a first generation F1 hybrid of a *S. lycopersicum* inbred line and a cherry-type *S. lycopersicum* inbred line; and the L1-shoot meristem layer preferably has the genotype of the L3- or L2-shoot meristem layer, preferably the L2-shoot meristem layer. All other variables may be as defined herein above. Preferably, within this embodiment plant C and L3-shoot meristem layer of the periclinal chimera plant have the genotype of a first generation F1 hybrid of the *Solanum lycopersicum* inbred line Ailsa Craig with the cherry-type *S. lycopersicum* inbred line.

In an embodiment of the method or use of the invention, plant A and the L2-shoot meristem layer of the periclinal chimera plant have the genotype of an inbred line of a beef variety of *Solanum lycopersicum*; plant B, more in particular the L2-shoot meristem layer of plant B, has the genotype of a *Solanum lycopersicum* inbred line; plant C and L3-shoot meristem layer of the periclinal chimera plant have the genotype of a first generation F1 hybrid of an *Solanum lycopersicum* inbred line with a cherry-type *S. lycopersicum* inbred line; and the L1-shoot meristem layer preferably has the genotype of the L2- or L3-shoot meristem layer, preferably the L2-shoot meristem layer. All other variables may be as defined herein above. Preferably, within this embodiment plant B is a plant of *Solanum lycopersicum* cv. MoneyMaker and/or plant C and L3-shoot meristem layer of the periclinal chimera plant have the genotype of a first generation F1 hybrid of the *Solanum lycopersicum* inbred line Ailsa Craig with the cherry-type *S. lycopersicum* inbred line.

In an embodiment of the method or use of the invention, plant A and the L2-shoot meristem layer of the periclinal chimera plant have the genotype of an inbred line of a beef variety of *Solanum lycopersicum*; plant B, more in particular the L2-shoot meristem layer of plant B, has the genotype of a *Solanum lycopersicum* inbred line; plant C and L1-shoot meristem layer of the periclinal chimera plant have the genotype of a first generation F1 hybrid of an *Solanum lycopersicum* inbred line with a cherry-type *S. lycopersicum* inbred line; and the L3-shoot meristem layer preferably has the genotype of the L1- or L2-shoot meristem layer, preferably the L2-shoot meristem layer. All other variables may be as defined herein above. Preferably, within this embodiment plant B is a plant of *Solanum lycopersicum* cv. MoneyMaker and/or plant C and L1-shoot meristem layer of the periclinal chimera plant have the genotype of a first generation F1 hybrid of the *Solanum lycopersicum* inbred line Ailsa Craig with the cherry-type *S. lycopersicum* inbred line.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum habrochaites* line; plant C and L1-shoot meristem layer of the periclinal chimera plant have the genotype of a first generation F1 hybrid of an *Solanum lycopersicum* inbred line with *S. habrochaites*; and the L3-shoot meristem layer preferably has the genotype of the L1- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L1-shoot meristem layer of the periclinal chimera plant have the genotype of a first generation F1 hybrid of the *Solanum lycopersicum* inbred line Ailsa Craig with *Solanum habrochaites* accession PI127826.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum habrochaites* line; plant C and L3-shoot meristem layer of the periclinal chimera plant have the genotype of a first generation F1 hybrid of an *Solanum lycopersicum* inbred line with *S. habrochaites*; and the L1-shoot meristem layer preferably has the genotype of the L3- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L3-shoot meristem layer of the periclinal chimera plant have the genotype of a first generation F1 hybrid of the *Solanum lycopersicum* inbred line Ailsa Craig with *Solanum habrochaites* accession P1127826.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum habrochaites* line; plant C and L1-shoot meristem layer of the periclinal chimera plant have the genotype of a first generation F1 hybrid of an *Solanum lycopersicum* inbred line with *S. pennellii*; and the L3-shoot meristem layer preferably has the genotype of the L1- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L1-shoot meristem layer of the periclinal chimera plant have the genotype of a first generation F1 hybrid of the *Solanum lycopersicum* inbred line Ailsa Craig with *Solanum pennellii* accession LA716.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum habrochaites* line; plant C and L3-shoot meristem layer of the periclinal chimera plant have the genotype of a first generation F1 hybrid of an *Solanum lycopersicum* inbred line with *S. pennellii*; and the L1-shoot meristem layer preferably has the genotype of the L3- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L3-shoot meristem layer of the periclinal chimera plant have the genotype of a first generation F1 hybrid of the *Solanum lycopersicum* inbred line Ailsa Craig with *Solanum pennellii* accession LA716. In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum pennellii* line; plant C and L1-shoot meristem layer of the periclinal chimera plant have the genotype of a first generation F1 hybrid of an *Solanum lycopersicum* inbred line with *S. habrochaites*; and the L3-shoot meristem layer preferably has the genotype of the L1- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L1-shoot meristem layer of the periclinal chimera plant have the genotype of a first generation F1 hybrid of the *Solanum lycopersicum* inbred line Ailsa Craig with *Solanum habrochaites* accession P1127826.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum pennellii* line; plant C and L3-shoot meristem layer of the periclinal chimera plant have the genotype of a first generation F1 hybrid of an *Solanum lycopersicum* inbred line with *S. habrochaites*; and the L1-shoot meristem layer preferably has the genotype of the L3- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L3-shoot meristem layer of the periclinal chimera plant have the genotype of a first generation F1 hybrid of the *Solanum lycopersicum* inbred line Ailsa Craig with *Solanum habrochaites* accession P1127826.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum pennellii* line; plant C and L1-shoot meristem layer of the periclinal chimera plant have the genotype of a first generation F1 hybrid of an *Solanum lycopersicum* inbred line with *S. pennellii*; and the L3-shoot meristem layer preferably has the genotype of the L1- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L1-shoot meristem layer of the periclinal chimera plant have the genotype of a first generation F1 hybrid of the *Solanum lycopersicum* inbred line Ailsa Craig with *Solanum pennellii* accession LA716.

In an embodiment of the method or use of the invention, plant A and the L2-shoot meristem layer of the periclinal chimera plant have the genotype of an inbred line of *Solanum lycopersicum*; plant B, more in particular the L2-shoot meristem layer of plant B, has the genotype of a *Solanum pennellii* line; plant C and L3-shoot meristem layer of the periclinal chimera plant have the genotype of a first generation F1 hybrid of an *Solanum lycopersicum* inbred line with *S. pennellii*; and the L1-shoot meristem layer preferably has the genotype of the L3- or L2-shoot meristem layer, preferably the L2-shoot meristem layer. All other variables may be as defined herein above. Preferably, within this embodiment plant A is a plant of *Solanum lycopersicum* cv. MoneyMaker and plant C and L3-shoot meristem layer of the periclinal chimera plant have the genotype of a first generation F1 hybrid of the *Solanum lycopersicum* inbred line Ailsa Craig with *Solanum pennellii* accession LA716.

The present invention also provides for seed having at least one altered, preferably improved, germination property as compared to the seed obtained or obtainable by crossing plant A with plant B. Said seed is obtainable from a method of the invention, i.e. by providing a periclinal chimera plant comprising an L2-shoot meristem layer that has the genotype of plant A, and an L1- and/or L3-shoot meristem layer that has the genotype of a third plant C, pollinating the periclinal chimera plant with pollen of plant B, and harvesting the seed thus obtained. Preferably said seed exhibits at least one of an altered (e.g. improved) seed density distribution, enhanced germination rate, enhanced germination capacity, improved germination uniformity, improved seed vigour, and seedling fresh weight compared to a seed derived from a cross of plant A with plant B, when tested under similar environmental conditions. Preferably, at least one of the germination properties is altered and/or improved, optionally multiple properties or altered and/or improved. The seed preferably has an integument or seed coat, which will have the genotype of the L1-shoot meristem layer of the periclinal chimera plant of the method of the invention. Seed obtained or obtainable by a method of the present invention, wherein the L2-shoot meristem layer has the genotype of plant A and the L1-shoot meristem layer has the genotype of plant C is recognized by its integument or seed coat having the genotype of plant C and its embryo having the genotype identical to a genotype obtained by a cross of plant A and plant B as defined herein.

The invention also provides for a periclinal chimera plant as defined herein in a method or use of the invention. Preferably, said periclinal chimera plant is for use in a method of the invention as defined herein. Preferably, the periclinal chimera plant for use in a method of the invention does not comprise a combination of L1-, L2- and L3-shoot meristem layers, wherein the L1-shoot meristem layer has a genotype of *S. pennellii* accession LA716, and wherein the L2- and L3-shoot meristem layers have a genotype of *S. lycopersicum* cultivar Heinz 1706. The invention also provides for a periclinal chimera as defined herein which is a fertilized periclinal chimera, i.e. comprising an embryo. Preferably, the embryo comprises a combination of the genotype of plant A and the genotype of plant B, similar to the genotype obtained from a cross with plant A and plant B.

The present invention also provides for seed production for rootstock varieties, rootstock varieties seed and rootstocks, wherein the seed is premium quality interspecific F1 hybrid seed. Commercial vegetable production is making increasing use of systems that utilize rootstock grafting. In such systems, the shoot of a cultivar (the scion, e.g. an F1 hybrid tomato variety) is grafted onto the root of a second cultivar (the rootstock). A rootstock itself is usually a F1 hybrid variety, especially bred for its excellent root properties to support the scion's growth and production. Rootstocks confer e.g. resistance to soil-borne pathogens, an optimal balance of vegetative vs. generative growth, resistance to cold soils, and extended longevity.

Because rootstocks do not need to meet quality parameters for marketable products (e.g. fruits, seeds or leaves), they can be bred with a much larger degree of freedom in their genetic make-up. It is possible, for example, to utilize the first generation F1 hybrid of a cultivated and a wild species, the latter providing immediate access to a wide array of genetic resistances to biotic and/or abiotic stresses. For example in tomatoes, most rootstocks are F1 hybrids from an interspecific cross of a wild species (e.g. *S. habrochaites, S. pennelli*) to a selected *S. lycopersicum* female.

While the benefits of such wide-hybrids are clear, a drawback is that the required crosses often suffer from a level of genetic incompatibility, which results in (very) poor quantity and quality of the F1 seeds. In tomato rootstock hybrids, incompatibilities that result in seed failure are usually ascribed to endosperm failure, leading to embryo malnourishment. The sporophytic maternal seed tissues (the integuments) play a role in endosperm failure. Variant expression levels of the integument-expressed gene TTG2 of *Arabidopsis* can amend interspecific crosses (Burkart-Waco D., Ngoa K., Dilkes B, Josefsson C and Comai L (2013) *Early disruption of maternal-zygotic interaction and activation of defense-like responses in Arabidopsis interspecific crosses*. Plant Cell 25 (6): 2037-2055). Commercial success of a rootstock hybrid is highly dependent on its germination properties, no less than on its properties as a root stock per se. This makes good germination one of the most highly sought-after traits in rootstock breeding. The current invention provides for such good germination properties.

In an exemplary embodiment, the current invention makes use of a periclinal chimera in which the L2 layer for instance is of *S. lycopersicum* (EE), whereas the L1 layer for instance is of hybrid genotype EW, derived from a cross of EE to a wild species with genotype WW. The genotype of L3 maybe be freely chosen. When such periclinal chimeras are crossed as females to male plants of pure genotype WW, plants germinating from the resulting seeds will be genotypically indistinguishable from a regular E×W cross, but with much improved germination properties. This opens the way to the production of premium quality interspecific F1 hybrid seed.

Within this disclosure, a *Solanum lycopersicum* plant variety Ailsa Craig can have accession number LA3579 and *Solanum lycopersicum* plant variety MoneyMaker can have e.g. accession LA2706.

EXAMPLES

Example 1: Improving Seed Germination of Beef Tomato F1 Hybrids

The germination properties of seeds of the F1 hybrid tomato variety XZ were improved. This variety is of the large beef type, and is produced by crossing a maternal (XX) and a paternal (ZZ) inbred line to produce tomato F1 hybrid seed.

A periclinal chimera was made of type {L3 (YY), L2 (XX), L1 (YY)}, wherein YY and XX denote diploidy (where X and Y are haploid). YY is the inbred tomato variety Ailsa Craig (accession LA3579). Periclinals were produced by first grafting YY scions onto XX rootstocks, followed by graft healing for 10 days. Graft junctions were then transversely cut, upon which callus growth and shoot regeneration occurred spontaneously. Among regenerated shoots, periclinal chimeras were selected visually, using the phenotypic markers xa (Szymkowiak, E. J., and Sussex, I. M. (1992), *The internal meristem layer (L3) determines floral meristem size and carpel number in tomato periclinal chimeras*, Plant Cell 4, pp. 1089-1100) and U (Powell et al., *Uniform ripening Encodes a Golden 2-like Transcription Factor Regulating Tomato Fruit Chloroplast Development*, Science 29 Jun. 2012: Vol. 336, Issue 6089, pp. 1711-1715) carried by the YY line. The semi-dominant marker xa was heterozygous, causing yellow leaves. The dominant U marker produces green shoulders on the fruit. Both markers are absent from XX. The chimera of the desired type was recognized by having leaves with a lighter green centre (L3 yellow) and darker green rims (green L2), and showing fruits with green shoulders. The L1 layer identity was determined to be YY by scoring the presence/absence in epidermal cells of a SNP marker that distinguished XX from YY. The chimera was very stable throughout development and during propagation from rooted cuttings of axillary shoots. Spontaneous L2 (XX) layer replacements, seen as yellow sectors in leaves and stems, were rare.

The breeding behavior of the chimera was analyzed using 518 SNP loci distributed over the genome (data not shown). The genotype of self-progeny (S1 seedlings, n=14) of the chimeras could not be distinguished from XX S1 seedlings from seed produced on a non-chimeric XX plant. This was further confirmed by segregation analyses of the xa marker. In 500 S1 seedlings from the chimeras, we have not observed a single yellow seedling. In contrast, self-progeny of non-chimeric YY (XA/xa heterozygotes) segregate 50% yellow seedlings.

These data showed that the chimera carried gametophytes from genotype X, and that the YY tissues only served a sporophytic role.

Seeds were produced from the chimera, as well as from non-chimeric XX and YY plants. To this end, 6 plants of each were grafted onto a rootstock of genotype XX, to equalize their root systems. They were either self-fertilized to produce line seed (S1) or cross fertilized with pollen from line ZZ to produce XZ hybrid seed (F1). All plants were grown in a regular greenhouse in the period April-August.

Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at 10 degrees Celsius/10% relative humidity, until use.

We defined and measured 5 germination properties of the seeds:
(a) density
(b) biomass
(c) germination rate
(d) germination capacity
(e) seedling fresh weight All measurements were taken in the following sequential way:

(a) Density

The density of a mature seed is a direct function of its physiological composition. It is mainly determined by the amount and the biochemical nature of metabolic compounds in endosperm and embryo, which occupy the space within the seed coat. Density (specific weight) was determined by liquid density separation in solutions of sucrose in water. ~500 seeds were sequentially passed through 0, 200 and 400 grams sucrose per liter water in a graduated cylinder. Seeds that sank in the lighter solution were collected and taken to the next. This resulted in 4 density fractions, from low to high: 0, 200, 400 and 400+. Fractions were thoroughly rinsed in tap water and dried for at least 72 hours on filter paper at room temperature. The number of seeds per fraction was counted, and the distribution over the density classes determined. Tests were replicated five times with independent 500-seed samples, totaling ~2500 seeds.

Figure 3A:
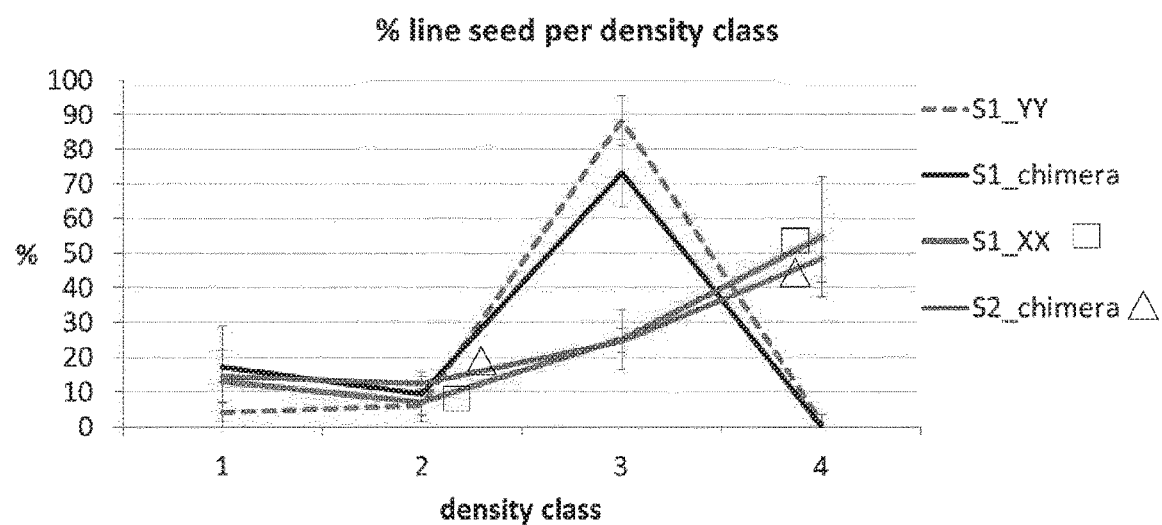
FIGS. 3A-3B. Density distribution of seeds. Error bars indicate the 95% confidence intervals. Non-overlapping error bars denote significantly different sample means (p=0.05). A: At density class "3", the lines represent from top to bottom: S1_YY (self-progeny of non-chimeric YY plant), S1-chimera (self-progeny of chimera), S1_XX (self-progeny of non-chimer XX plant), and S2_chimera (self-progeny of S1-chimera). B: At density class "3", the lines represent from top to bottom: F1_XX (progeny of the cross-fertilization of the non-chimeric plant XX with line ZZ), F1_chimera (progeny of the cross-fertilization of the chimera with line ZZ).
Figure 3B:
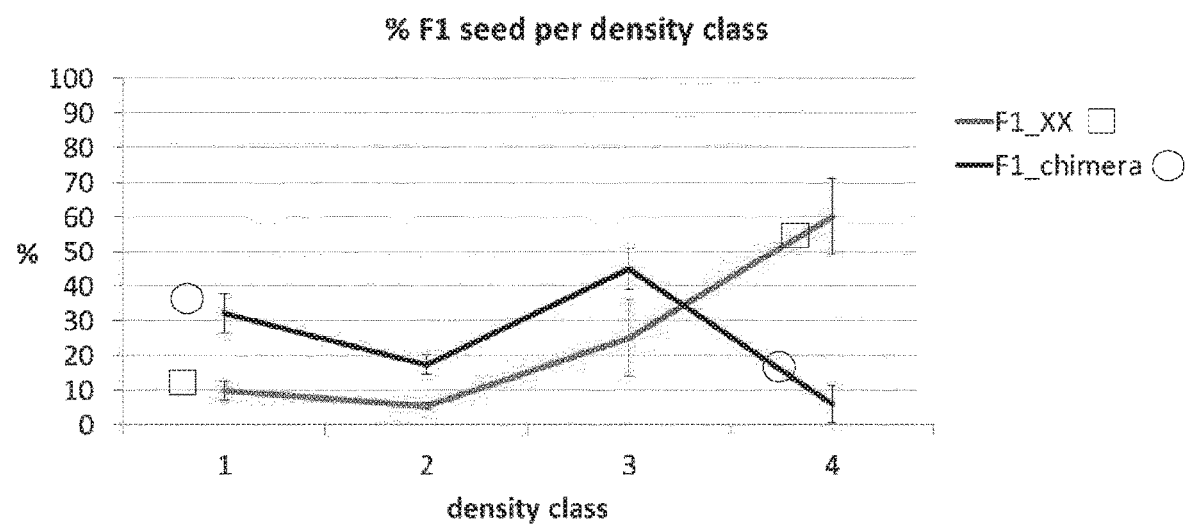

As shown in FIG. 3A, S1 seeds of the chimera had a density distribution identical to that of YY S1 seeds, but very different from XX S1 seeds. Because the chimera-derived S1 seeds and those of XX are genetically identical in embryo and endosperm, it must be concluded that the difference in density had been physiologically imparted onto the seeds by the YY sporophyte. This was confirmed by analyzing S2 seeds of the chimera-derived S1 plants. The S2 seeds, having been grown on an XX sporophyte, had a density distribution identical to that of XX (FIG. 3A). The same pattern was observed for F1 hybrid seeds (FIG. 3B), showing that the seed density trait imparted by YY is independent of the genotype of embryo and endosperm.

(b) Biomass

Biomass is a function of the total amount of biological material present within the seed, independent of its density. Biomass accumulation in the seed is ultimately limited by the sporophyte, as embryo and endosperm are heterotrophic. Total biomass of dried and counted seeds from each of the density fractions from section (a) above and from each of the five replicates was measured on a precision balance. Data were converted into the average mass per individual seed.

Figure 4A:
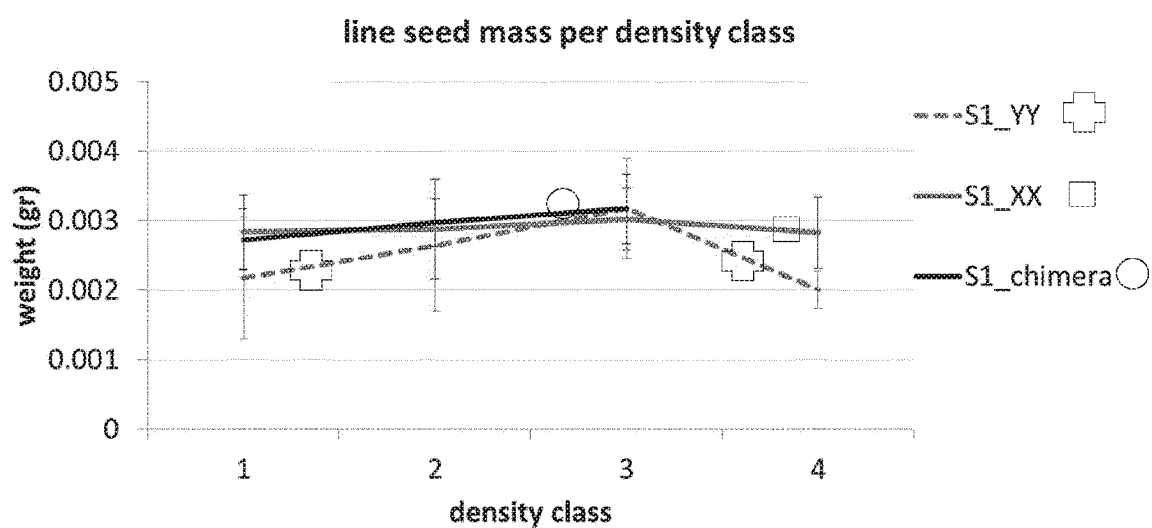
FIGS. 4A-4B. Biomass distribution of seeds in the different density classes. Error bars indicate the 95% confidence intervals. Non-overlapping error bars denote significantly different sample means (p=0.05). A: At density class "1", the lines represent from top to bottom: S1_XX, S1_chimera, S1_YY. B: At density class "3", the lines represent from top to bottom: F1_chimera, F1_XX.
Figure 4B:
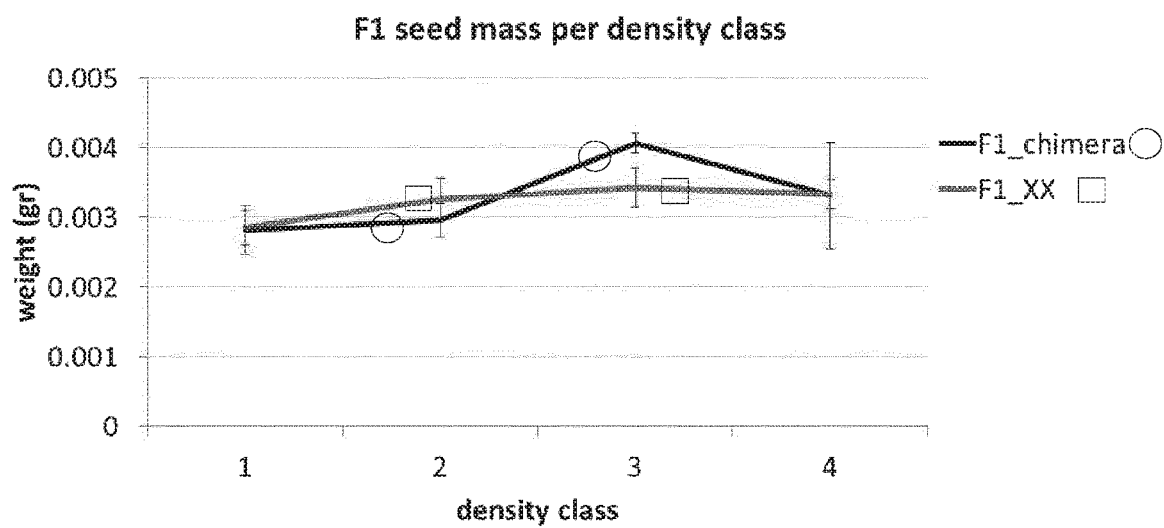

As shown in FIG. 4A, biomass of S1 seed did not differ much among the 4 density classes and among genotypes. The tendency was that seed in density class 3 had the largest biomass. This was clearest for the pure YY plants, in which a steep weight decline was seen from density class 3 to density class 4. This YY pattern was conferred onto F1 seeds from the chimera (FIG. 4B). In addition, chimera F1 seeds were significantly heavier in class 3 than were F1 seeds from XX (FIG. 4B).

(c) Germination Rate

Germination rate was determined in vitro by sowing 100 seeds in a gridded array on moistened (tap water) filter paper in a sealed petridish, followed by incubation under 16/24 hours of white light in a growth chamber at 23 degrees Celsius. Germination was scored in 24 hour intervals as the visible emergence of a radicle, over a period of 7 days. The rate was then calculated according to the formula: rate=(#1/1)+(#2/2)+ . . . +(#7/7), wherein #1 is the number of germinated seeds after 24 hours, #2 the number of germinated seeds after 48 hours, etc. The higher the rate number, the quicker the emergence of radicles. Tests were replicated nine times with independent 100-seed samples, totalling 900 seeds.

Figure 5A:
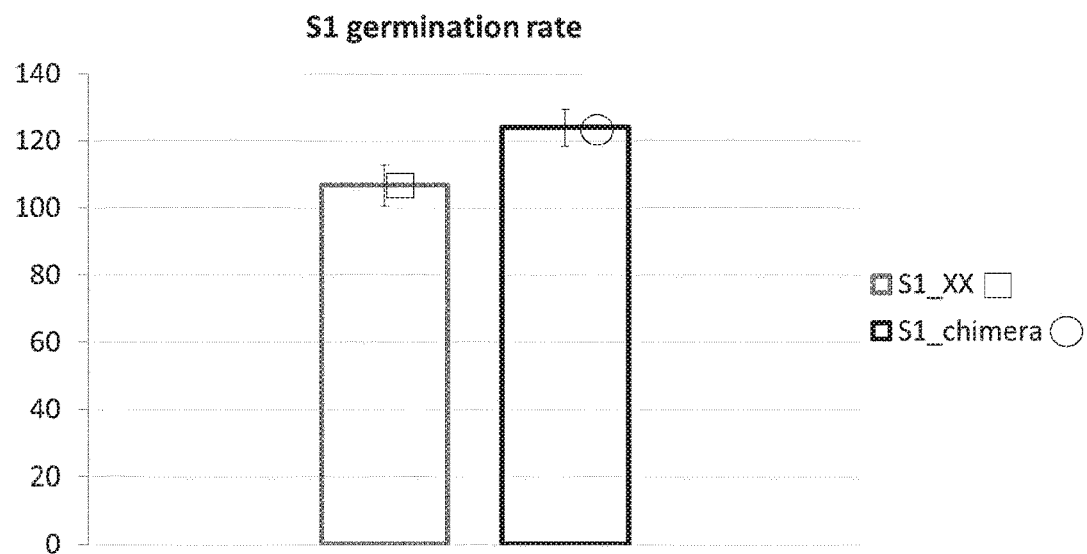
FIGS. 5A-5B. Germination rate of seeds. Error bars indicate the 95% confidence intervals. Non-overlapping error bars denote significantly different sample means (p=0.05). A: left column represents S1_XX, right column represents S1_chimera. B: left column represents F1_XX, right column represents F1_chimera.
Figure 5B:
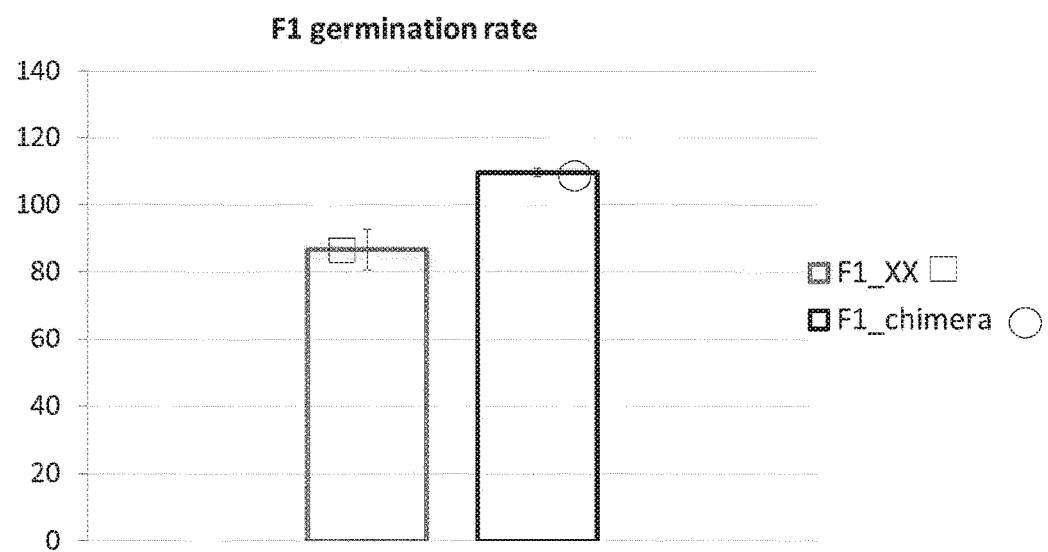

FIG. 5 shows the results of in vitro germination rate tests of S1 and F1 seeds from the chimera and from XX control plants. Seeds were taken only from density class 3 (chimera derived) or density class 4 (XX derived) because these represent their respective norms. Seeds of YY plants were not included, because they carry an YY-genotype embryo and are therefore not directly comparable. From FIG. 5 it is clear that the chimera produced seeds with a higher germination rate, both for 51 (FIG. 5A) and F1 (FIG. 5B) seeds. This rate gain was particularly clear for F1 seeds, which markedly germinated the control in the first 2 days after sowing (see FIGS. 6A and 6B). Because embryos and endosperm from the chimera and from the XX control are genetically identical, it must be concluded that the germination rate difference had been conferred by sporophyte YY.

(d) Germination Capacity

Germination capacity was measured in vitro in the same arrays as described under section (c) above, by scoring the total number of seeds (%) that had germinated after 7 days. In addition, germination capacity was measured in vivo by sowing 120 seeds (density class 3 for the chimera, density class 4 for XX) in 12 groups of 10 in a gridded array onto soil, covering them by a thin layer of fine soil, and mild watering. For in vivo germination, seeds were also manually selected for size, such that the largest seeds were sown. The number of germinated seedlings was scored after 7 days in a greenhouse.

Figure 6A:
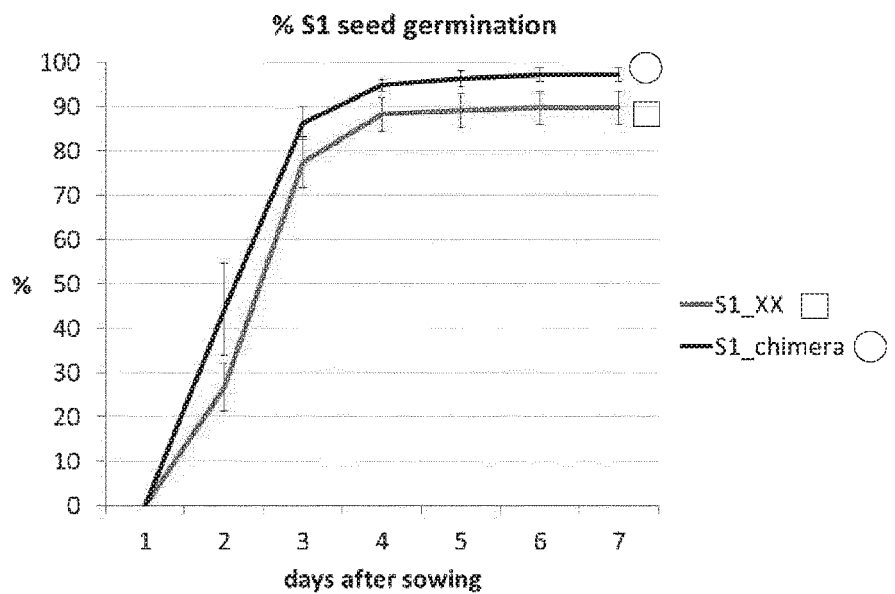
FIGS. 6A-6C. Panels A and B. In vitro germination capacity. Error bars indicate the 95% confidence intervals. Non-overlapping error bars denote significantly different sample means (p=0.05). A: top line represents S1_chimera, bottom line represents S1_XX. B: top line represents F1_chimera, bottom line represents F1_XX.
Figure 6B:
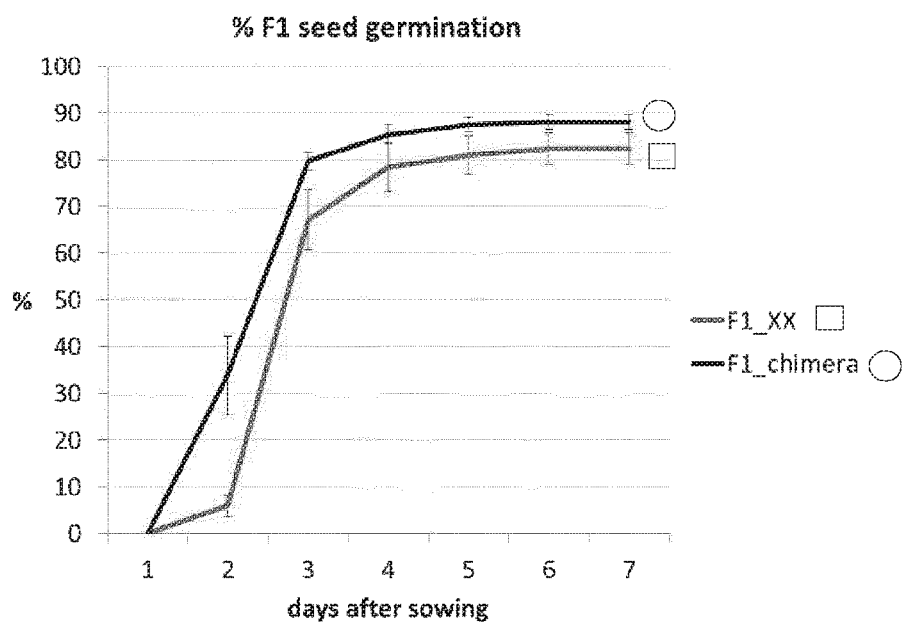
Figure 6C:
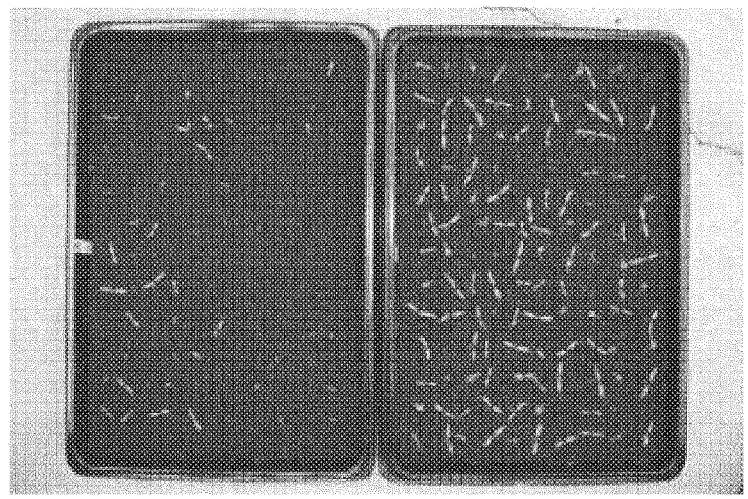

Results are given in FIG. 6. Germination capacity in vitro was significantly higher for both S1 (FIG. 6A) and F1 (FIG. 6B) seed of the chimera, compared to the XX control plant. F1 seeds had an intrinsically lower capacity than 51. The difference in germination capacity was particularly clear under in vivo conditions. After 7 days, chimera-derived seeds had germinated uniformly to 98%, whereas the control showed poor and irregular germination (FIG. 6C).

(e) Seedling Fresh Weight

Seedling shoot fresh weight was measured by first transferring 20 randomly selected germinated seeds (germinated on the second day of the procedure described in section (c)), to a flat filled with soil. At picking, they mostly had only an emerged root, sometimes with the first signs of the emerging hypocotyl. They were laid onto the soil surface, covered with a thin layer of fine soil, and watered. Care was taken not to damage the young seedlings during transfer. Measurements were done after 7 days of growth under ambient conditions in a greenhouse. Whole-seedling-shoots (until the hypocotyl-root junction) were freshly harvested and weighed on a precision balance.

As can be seen from FIG. 7, S1 seedlings (FIG. 7A) and F1 seedlings (FIG. 7B) from the chimera were significantly heavier than the control. This difference was particularly clear in the F1 seeds. Heavy seedlings most likely result either from copious food reserves in the mature seed, and/or from enhanced growth of the embryo during development, enabled by the supplies from the YY sporophyte.

The above-shown data show that a remarkable change in various seed germination aspects (a-e) has occurred under the influence of a sporophytic genotype that was genetically unrelated to the embryo and endosperm. The result was improved seed quality, when measured as rate and capacity for germination under different environmental conditions, and as seedling vigor.

Example 2: Improved Seed Germination in *S. lycopersicum*×*S. Pennellii* F1 Hybrids The germination properties of tomato seeds from the interspecific F1 hybrid variety TP were improved. This variety is produced by crossing a maternal inbred line TT of *S. lycopersicum* to a paternal line PP of *S. pennellii*.

A periclinal chimera was made of type {L3 (TT), L2 (TT), L1 (EP)}, wherein TT and EP denote diploidy (where T and E and P are haploid). TT is a standard inbred tomato (*S. lycopersicum*) variety. EP is a first generation F1 hybrid of *S. lycopersicum* inbred line EE (cv Ailsa Craig, accession LA3579), and a *S. pennellii* line PP (accession LA716). Periclinals were produced by first grafting EP scions onto TT rootstocks, followed by graft healing for 10 days. Graft junctions were then transversely cut, upon which callus growth and shoot regeneration occurred spontaneously. Among regenerated shoots, periclinal chimeras were selected visually, using the phenotypic marker xa plus high trichome density carried by EP scions. The semi-dominant marker xa, in heterozygous condition, causes yellow leaves when present in L2 and/or L3. The chimera of the desired type was recognized by having green leaves (L2 and L3 of TT), plus a high trichome density (L1 of EP). The chimera was very stable throughout development and during propagation from rooted cuttings of axillary shoots, as judged by the complete absence of spontaneous invasions of L1 cells into L2, which would have been seen as yellow sectors in leaves and stems. The breeding behavior of the chimera was analyzed using segregation analyses of the xa marker. In 500 seedlings of the chimera, from a backcross to PP, we have not observed a single yellow seedling. These data showed that the chimera carried gametophytes exclusively from genotype T, and that the EP tissues only served a sporophytic role. Because the L1 layer is well known to give rise to the integuments of the ovule and later to the seed coat of the mature seed, the sporophytic role of EP in seed development of the chimera has been that of integuments and seed coat.

Interspecific TP F1-hybrid seeds were produced from the chimera, as well as from non-chimeric TT plants. To this end, 6 plants of each were grafted onto a rootstock of genotype TT, to equalize their root systems. They were cross fertilized with pollen from line PP to produce TP hybrid seed (F1). All plants were grown in a regular greenhouse in the period April-August. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at 10 degrees Celsius/10% relative humidity, until use.

We defined and measured 3 germination properties of the seeds:
(a) density
(b) germination rate
(c) germination capacity All measurements were taken in the following sequential way:
(a) Density The density of a mature seed is a direct function of its physiological composition. It is mainly determined by the amount and the biochemical nature of metabolic compounds in endosperm and embryo, which occupy the space within the seed coat. Density (specific weight) was determined by liquid density separation in solutions of sucrose in water. ~500 seeds were sequentially passed through 0, 200 and 400 grams sucrose per liter water in a graduated cylinder. Seeds that sank in the lighter solution were collected and taken to the next. This resulted in 4 density fractions, from low to high: 0, 200, 400 and 400+. Fractions were thoroughly rinsed in tap water and dried for at least 72 hours on filter paper at room temperature. The number of seeds per fraction was counted, and the distribution over the density classes determined.

As shown in FIG. 8, interspecific F1 seeds made from crosses of non-chimeric TT to PP had a density distribution very different from the chimera crossed to PP. In contrast to the chimeric cross, the non-chimeric cross had a high proportion of poorly filled, light seeds. Because the genotypes of embryo and endosperm in these two crosses are identical, it must be concluded that the difference in density distribution had been physiologically imparted onto the seeds by the EP sporophyte. A high proportion of poorly filled seeds is characteristic of the cross *S. lycopersicum*×*S. pennellii*, and is a manifestation of a mild interspecific crossing barrier between these species. The chimera significantly relaxed this barrier.

(b) Germination Rate

Germination rate was determined in vitro by sowing 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. The rate was then calculated according the formula: rate=(#1/1)+(#2/2)+ . . . +(#7/7), wherein #1 is the number of germinated seeds after 24 hours, #2 the number of germinated seeds after 48 hours, etc. The higher the rate number, the quicker the emergence of radicles. Tests were done with a 100-seed sample.

FIG. 9 shows the results of in vitro germination rate tests of F1 seeds from the chimera and from TT control plants. Only raw seeds batches were sown, i.e. they were not density fractionated before sowing. From FIG. 9 it is clear that the chimera produced seed batches with a higher germination rate. Because embryos and endosperm from the chimera and from the TT control are genetically identical, it must be concluded that the germination rate difference had been conferred physiologically by sporophyte EP. Retarded seed germination is characteristic of the cross *S. lycopersicum*×*S. pennellii*, and is a manifestation of a mild interspecific crossing barrier between these species. The chimera significantly overcomes this barrier.

(c) Germination Capacity

Germination capacity was measured in vitro in the same arrays as described under section (b) above, by scoring the total number of seeds (%) that had germinated after 10 days. Results are given in FIG. 10. Germination capacity in vitro was higher for seed of the chimera, compared to the TT control plant.

Example 3: Improved Seed Germination in *S. lycopersicum*×*S. Habrochaites* F1 Hybrids Germination properties of tomato seeds from the interspecific F1 hybrid variety TH were improved. This variety is produced by crossing a maternal inbred line TT of *S. lycopersicum* to a paternal line HH from *S. habrochaites*.

A periclinal chimera was made of type {L3 (TT), L2 (TT), L1 (EP)}, wherein TT and EP denote diploidy (where T and E and P are haploid). TT is a standard inbred tomato (*S. lycopersicum*) variety. EP is a first generation F1 hybrid of a standard *S. lycopersicum* inbred line EE (cv. Ailsa Craig accession LA3579), and a *S. pennellii* line PP (accession LA716). Periclinals were produced by first grafting EP scions onto TT rootstocks, followed by graft healing for 10 days. Graft junctions were then transversely cut, upon which callus growth and shoot regeneration occurred spontaneously. Among regenerated shoots, periclinal chimeras were selected visually, using the phenotypic marker xa plus high trichome density carried by EP scions. The semi-dominant marker xa, present in heterozygous condition, causes yellow leaves when present in L2 and/or L3. The chimera of the desired type was recognized by having green leaves (L2 and L3 of TT), plus a high trichome density (L1 of EP). The chimera was very stable throughout development and during propagation from rooted cuttings of axillary shoots, as judged by the complete absence of spontaneous invasions of L1 cells into L2, which would have been seen as yellow sectors in leaves and stems. The breeding behavior of the chimera was analyzed using segregation analyses of the xa marker. In 500 seedlings of the chimera, from a backcross to PP, we have not observed a single yellow seedling. These data showed that the chimera carried gametophytes exclusively from genotype T, and that the EP tissues only served a sporophytic role. Because the L1 layer is well known to give rise to the integuments of the ovule and later to the seed coat of the mature seed, the sporophytic role of EP in seed development of the chimera has been that of integuments and seed coat.

The chimera, as well as non-chimeric TT control plants were cross fertilized with pollen from *S. habrochaites* accession P1127826, denoted as HH, to produce TH hybrid seed (F1). All plants were grown in a regular greenhouse in the period April-August. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

We defined and measured 3 germination properties of the seeds: (a) specific weight (b) germination rate (c) germination capacity, All measurements were taken in the following sequential way:

(a) Specific Weight

The density of a mature seed is a direct function of its physiological composition. It is mainly determined by the amount and the biochemical nature of metabolic compounds in endosperm and embryo, which occupy the space within the seed coat. Specific weight was determined by liquid density separation in solutions of sucrose in water. ~500 seeds were sequentially passed through 0, 200 and 400 grams sucrose per liter water in a graduated cylinder. Seeds that sank in the lighter solution were collected and taken to the next. This resulted in 4 density fractions, from low to high: 0, 200, 400 and 400+. Fractions were thoroughly rinsed in tap water and dried for at least 72 hours on filter paper at room temperature. The number of seeds per fraction was counted, and the distribution over the density fractions determined.

As shown in FIG. 11, interspecific F1 seeds made from control crosses of non-chimeric TT to HH had a density distribution different from the chimera crossed to HH. The control cross had a higher proportion of poorly filled, light seeds. Because the genotypes of embryo and endosperm in these two crosses are identical, it must be concluded that the difference in density distribution had been physiologically imparted onto the seeds by the EP sporophyte. A high proportion of poorly filled seeds is characteristic of the cross *S. lycopersicum*×*S. habrochaites*, and is a manifestation of an interspecific crossing barrier between these species. The EP sporophytic tissues in the chimeric cross corrected this.

(b) Germination Rate

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. The rate was then calculated according to the formula: rate=(#1/1)+(#2/2)+ . . . +(#7/7), wherein #1 is the number of germinated seeds after 24 hours, #2 the number of germinated seeds after 48 hours, etc. The higher the rate number, the quicker the emergence of radicles. Tests were done with three 100-seed samples.

FIG. 12 shows the results of germination rate tests of F1 seeds produced on the chimera and on TT control plants. Only raw seeds batches were sown, i.e. they were not density fractionated before sowing. From FIG. 12 it is clear that the chimera produced seed batches with a higher germination rate. Because embryos and endosperm from the chimera and from the TT control are genetically identical, it must be concluded that the germination rate difference had been conferred physiologically by sporophyte EP. Very poor seed germination is characteristic of the cross *S. lycopersicum*×*S. habrochaites*, and is a manifestation of an interspecific crossing barrier between these species. The EP sporophytic tissues in the chimeric cross relaxed this barrier.

(c) Germination Capacity

Germination capacity was measured in vitro in the same arrays as described under section (b) above, by scoring the total number of seeds (%) that had germinated after 7 days. Results are given in FIG. 13. Germination capacity in vitro was much higher for seed made on the chimera, compared to seed made on the TT control plant.

Example 4: Improved Seed Germination of Beef Tomato Inbred Seeds

Germination properties of inbred seeds from the beef variety BB were improved. This variety is produced by self-fertilization of the inbred line BB of *S. lycopersicum*.

A periclinal chimera was made of type {L3 (BB), L2 (BB), L1 (ER)}, wherein BB and ER denote diploidy (where B and E and R are haploid). ER is a first generation F1 hybrid of *S. lycopersicum* inbred line EE (cv. Ailsa Craig accession LA3579), and the cherry-type *S. lycopersicum* inbred line RR. Periclinals were produced by first grafting ER scions onto BB rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the ER hybrid), followed by selection of fully green axillary branches. Green branches were genotyped with a SNP marker that distinguished BB from EE. The presence of an EE SNP indicated the shoot to be a periclinal chimera carrying an L1 layer of genotype ER over the L2 and L3 layers of BB. The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric BB control plants were self-fertilized. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 8 days. As can be seen FIG. 14, the chimera produced seeds with a strongly improved germination speed and capacity.

Example 5: Improved Seed Germination of Beef Tomato Inbred Seeds

Germination properties of inbred seeds from the beef variety BM were improved. This variety is produced by self-fertilization of the inbred line BB of *S. lycopersicum*.

A periclinal chimera was made of type {L3 (ER), L2 (BB), L1 (BB)}, wherein BB and ER denote diploidy (where B and E and R are haploid). ER is a first generation F1 hybrid of standard *S. lycopersicum* inbred line EE (cv. Ailsa Craig accession LA3579), and the cherry-type *S. lycopersicum* inbred line RR. Periclinals were produced by first grafting ER scions onto BB rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the ER hybrid). Axillary branches were selected with the central parts of the leaf being somewhat lighter green in colour, and with darker green outer rims. These branches were genotyped with a SNP marker that distinguished BB from EE. Genotyping was done on DNA from dissected tissues from the pith of the stem (L3 derived) and from thin epidermal peels (L1). The presence of an EE SNP in the first and its absence in the latter indicated the shoot to be a periclinal chimera carrying an L3 layer of genotype ER under the L2 and L1 layers of BB. The chimera was very stable throughout development and during propagation from rooted cuttings of axillary shoots, as judged by the absence of spontaneous invasions of L3 cells into L2, which would have been seen as full yellow sectors in otherwise green tissues.

The chimera, as well as non-chimeric BB control plants were self-fertilised. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 8 days. As can be seen FIG. 15, the chimera produced seeds with a very strongly improved germination speed and capacity.

Example 6: Improved Seed Germination of F1 Seeds from a Beef-Type Mother Plant Germination properties of tomato seeds from the F1 hybrid variety BM were improved. This variety is produced by crossing a maternal beef-type inbred line BB of *S. lycopersicum* to a paternal line MM (cv. MoneyMaker) from *S. lycopersicum*.

A periclinal chimera was made of type {L3 (ER), L2 (BB), L1 (BB)}, wherein BB and ER denote diploidy (where B and E and R are haploid). ER is a first generation F1 hybrid of standard *S. lycopersicum* inbred line EE (cv. Ailsa Craig accession LA3579), and the cherry-type *S. lycopersicum* inbred line RR. Periclinals were produced by first grafting ER scions onto BB rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the ER hybrid). Axillary branches were selected with the central parts of the leaf being somewhat lighter green in colour, and with darker green outer rims. These branches were genotyped with a SNP marker that distinguished BB from EE. Genotyping was done on DNA from dissected tissues from the pith of the stem (L3 derived) and from thin epidermal peels (L1). The presence of an EE SNP in the first and its absence in the latter indicated the shoot to be a periclinal chimera carrying an L3 layer of genotype ER under the L2 and L1 layers of BB. The chimera was very stable throughout development and during propagation from rooted cuttings of axillary shoots, as judged by the absence of spontaneous invasions of L3 cells into L2, which would have been seen as full yellow sectors in otherwise green tissues.

The chimera, as well as non-chimeric BB control plants were cross fertilized with pollen from MM to produce BM hybrid seed (F1). Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 8 days. As can be seen FIG. 16, the chimera produced seeds with a strongly improved germination speed and capacity.

Example 7: Improved Seed Germination of Interspecific *S. lycopersicum*×*S. Habrochaites* F1 Seeds Germination properties of tomato seeds from the F1 hybrid variety MH2 were improved. This variety is produced by crossing a maternal inbred line MM (MoneyMaker) of *S. lycopersicum* to a paternal line H2H2 from *S. habrochaites*.

A periclinal chimera was made of type {L3 (MM), L2 (MM), L1 (EH1)}, wherein MM and EH1 denote diploidy (where M and E and H1 are haploid). EH1 is a first generation F1 hybrid of *S. lycopersicum* inbred line EE (cv. Ailsa Craig accession LA3579), and *S. habrochaites* accession PI127826.

Periclinals were produced by first grafting EH1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EH1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EH1 over the L2 and L3 layers of MM. Such chimeras could in addition be easily recognized by the distinct trichome structure of the EH1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. habrochaites* genotype H2 (accession LA1625) to produce MH2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 17, the chimera produced seeds with a strongly improved germination speed and capacity.

Example 8: Improved Seed Germination of Interspecific *S. lycopersicum×S. Habrochaites* F1 Seeds Germination properties of tomato seeds from the F1 hybrid variety MH2 were improved. This variety is produced by crossing a maternal inbred line MM (MoneyMaker) of *S. lycopersicum* to a paternal line H2H2 from *S. habrochaites*.

A periclinal chimera was made of type {L3 (MM), L2 (MM), L1 (EP1)}, wherein MM and EP1 denote diploidy (where M and E and P1 are haploid). EP1 is a first generation F1 hybrid of *S. lycopersicum* inbred line EE (cv. Ailsa Craig accession LA3579), and *S. pennellii* accession LA716. Periclinals were produced by first grafting EP1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EP1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EP1 over the L2 and L3 layers of MM. Such chimeras could in addition be easily recognized by the distinct trichome structure of the EP1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. habrochaites* genotype H2 (accession LA1625) to produce MH2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 18, the chimera produced seeds with a strongly improved germination speed capacity.

Example 9: Improved Seed Germination of Interspecific *S. lycopersicum×S. Pennellii* F1 Seeds Germination properties of tomato seeds from the F1 hybrid variety MP2 were improved. This variety is produced by crossing a maternal inbred line MM (MoneyMaker) of *S. lycopersicum* to a paternal line P2P2 from *S. pennellii*.

A periclinal chimera was made of type {L3 (MM), L2 (MM), L1 (EH1)}, wherein MM and EH1 denote diploidy (where M and E and H1 are haploid). EH1 is a first generation F1 hybrid of *S. lycopersicum* inbred line EE (cv. Ailsa Craig accession LA3579), and *S. habrochaites* accession PI127826. Periclinals were produced by first grafting EH1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EH1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EH1 over the L2 and L3 layers of MM. Such chimeras could in addition be easily recognized by the distinct trichome structure of the EH1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. pennellii* genotype P2 (accession LA1809) to produce MP2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 19, the chimera produced seeds with a strongly improved germination speed and capacity.

Example 10: Improved Seed Germination of Interspecific *S. lycopersicum*×*S. Pennellii* F1 Seeds Germination properties of tomato seeds from the F1 hybrid variety MP2 were improved. This variety is produced by crossing a maternal inbred line MM (MoneyMaker) of *S. lycopersicum* to a paternal line P2P2 from *S. pennellii*.

A periclinal chimera was made of type {L3 (MM), L2 (MM), L1 (EP1)}, wherein MM and EP1 denote diploidy (where M and E and P1 are haploid). EP1 is a first generation F1 hybrid of *S. lycopersicum* inbred line EE (cv. Ailsa Craig accession LA3579), and *S. pennellii* accession LA716. Periclinals were produced by first grafting EP1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EP1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EP1 over the L2 and L3 layers of MM. Such chimeras could in addition be easily recognized by the distinct trichome structure of the EP1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. pennellii* genotype P2 (accession LA1809) to produce MP2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 20, the chimera produced seeds with a strongly improved germination speed capacity.

Example 11: Improved Seed Germination of Interspecific *S. lycopersicum*×*S. Pennellii* F1 Seeds Germination properties of tomato seeds from the F1 hybrid variety MP3 were improved. This variety is produced by crossing a maternal inbred line MM (MoneyMaker) of *S. lycopersicum* to a paternal line P3P3 from *S. pennellii*.

A periclinal chimera was made of type {L3 (MM), L2 (MM), L1 (EH1)}, wherein MM and EH1 denote diploidy (where M and E and H1 are haploid). EH1 is a first generation F1 hybrid of *S. lycopersicum* inbred line EE (cv. Ailsa Craig accession LA3579), and *S. habrochaites* accession PI127826. Periclinals were produced by first grafting EH1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EH1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EH1 over the L2 and L3 layers of MM. Such chimeras could in addition be easily recognized by the distinct trichome structure of the EH1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. pennellii* genotype P3 (accession LA2657) to produce MP3 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 21, the chimera produced seeds with a strongly improved germination speed and capacity.

The invention claimed is:
1. A method for the production of seed with an embryo genotype identical to seed obtained by crossing a first plant A with a second plant B, wherein one or more germination properties of the seed are improved as compared to seed obtained by crossing the first plant A with the second plant B, the method comprising:
  (a) making a periclinal chimera plant comprising an L2-shoot meristem layer that has the genotype of plant A, and an L1- and/or L3-shoot meristem layer that has the genotype of a third plant C;
  (b) pollinating the periclinal chimera plant with pollen of a plant having an L2-shoot meristem layer that has the genotype of plant B; and
  (c) selecting seeds having one or more improved germination properties selected from the group consisting of germination capacity, uniformity of germination, germination rate, and seedling fresh weight,
  wherein the first plant A, the second plant B, and the third plant C are [plants of the same genus] from species belonging to the genus *Solanum*, and wherein the genotypes of plants A and C differ from each other.

2. The method according to claim 1, further comprising:
d) allowing the seed obtained in c) to germinate.

3. The method according to claim 1, further comprising:
e) assessing at least one germination property of the seed obtained in c).

4. The method according to claim 1, wherein plant C is a hybrid.

5. The method according to claim 1, wherein in the periclinal chimera plant of (a), the genotype of plant C comprises part of the genotype of plant A and/or plant B.

6. The method according to claim 1, wherein in the periclinal chimera plant of (a), the genotype of the L1- and/or L3-shoot meristem layer comprises part of the genotype of plant B.

7. The method according to claim 1, wherein the genotype of plant A is identical to the genotype of plant B.

8. The method according to claim 7, wherein in (b) the periclinal chimera plant is self-fertilized.

9. The method according to claim 1, wherein one or more of plants A, B, and C are hybrids of species of the same genus.

10. The method according to claim 1, wherein plants A, B, and C are plants of the same species.

11. The method according to claim 1, wherein plants A, B, and C are from species of *Solanum lycopersicum, Solanum pennellii, Solanum habrochaites, Solanum pimpinellifolium*, or hybrids thereof.

* * * * *